(12) United States Patent
Ophardt

(10) Patent No.: US 11,702,274 B2
(45) Date of Patent: *Jul. 18, 2023

(54) FLUID STORAGE RESERVOIR

(71) Applicant: OP-Hygiene IP GmbH, Niederbipp (CH)

(72) Inventor: Heiner Ophardt, Arisdorf (CH)

(73) Assignee: OP-HYGIENE IP GmbH, Niederbipp (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/464,133

(22) Filed: Sep. 1, 2021

(65) Prior Publication Data
US 2021/0394995 A1 Dec. 23, 2021

Related U.S. Application Data

(63) Continuation of application No. 16/176,036, filed on Oct. 31, 2018, now Pat. No. 11,136,182.

(30) Foreign Application Priority Data

Nov. 6, 2017 (CA) .................................. CA 2984761

(51) Int. Cl.
*B65D 83/00* (2006.01)
*A61L 2/18* (2006.01)
(Continued)

(52) U.S. Cl.
CPC ............ *B65D 83/0005* (2013.01); *A61L 2/18* (2013.01); *B65D 81/24* (2013.01); *B65D 83/0055* (2013.01); *B65D 85/70* (2013.01)

(58) Field of Classification Search
CPC ....... A47K 5/14; A47K 5/1207; A61L 2/0088; A61L 2/18; A61L 2/26; A61L 2202/12;
(Continued)

(56) References Cited

U.S. PATENT DOCUMENTS 3,095,122 A 6/1963 Lewiecki
3,225,967 A * 12/1965 Heimgartner .......... B65D 83/62
222/206

(Continued)

FOREIGN PATENT DOCUMENTS

DE 19847968 4/2000
FR 2710036 3/1995
KR 20120001027 2/2012

*Primary Examiner* — Chun Hoi Cheung
(74) *Attorney, Agent, or Firm* — Thorpe North & Western, LLP; Peter M. de Jonge; Kurt Hendricks

(57) ABSTRACT

A method of storing a product that contains a volatile component within a fluid storage reservoir formed with enclosing walls having a permeability that permits limited passage of the volatile component from the storage reservoir to the atmosphere, preferably with the method increasing the shelf life of the product stored, and a fluid storage reservoir with a first container containing the fluid product to be dispensed including the volatile component and a second container containing a sacrifice material including the same volatile component with an intermediate transfer wall shared by both the first container and the second container for transfer of the volatile component between the first container and the second container. The product preferably is a surface cleaner or a hand sanitizer including 30 to 95% ethanol.

20 Claims, 15 Drawing Sheets

(51) Int. Cl.
  *B65D 85/00* (2006.01)
  *B65D 81/24* (2006.01)
(58) Field of Classification Search
  CPC ....... A61L 2202/17; B65D 1/40; B65D 85/70; B65D 83/0005; B65D 83/0055; B65D 81/24; B05B 11/00414
  USPC .................. 222/105; 206/213.1; 220/459.01, 220/459.05, 459.06
  See application file for complete search history.

(56) References Cited

U.S. PATENT DOCUMENTS

| | | | |
|---|---|---|---|
| 3,910,449 A | 10/1975 | Gezari | |
| 3,992,003 A | 11/1976 | Visceglia | |
| 4,585,149 A * | 4/1986 | Zulauf | B65D 81/3244 222/144.5 |
| 5,282,552 A | 2/1994 | Ophardt | |
| 5,505,342 A * | 4/1996 | Okamura | B65D 83/0055 222/105 |
| 5,630,531 A | 5/1997 | Gaucher | |
| 7,815,076 B2 | 10/2010 | Ophardt | |
| 8,365,954 B2 | 2/2013 | Ophardt | |
| 8,479,950 B2 | 7/2013 | Ophardt | |
| 8,579,137 B2 | 11/2013 | Lustenberger | |
| 2004/0000562 A1 | 1/2004 | Gantner | |
| 2005/0274737 A1 | 12/2005 | Krause | |
| 2009/0212071 A1 | 8/2009 | Tom | |
| 2010/0101426 A1 | 4/2010 | De Mei | |
| 2010/0264165 A1 | 10/2010 | Hansen | |
| 2011/0139810 A1 | 6/2011 | Lee | |
| 2013/0193164 A1 | 8/2013 | Tom | |
| 2014/0252032 A1 | 9/2014 | Corbett | |
| 2017/0266680 A1 | 9/2017 | Ophardt | |

* cited by examiner

FLUID STORAGE RESERVOIR

RELATED APPLICATION

This application is a continuation of co-pending U.S. patent application Ser. No. 16/176,036 filed Oct. 31, 2018 and claims the benefit of 35 U.S.C. 120.

SCOPE OF THE INVENTION

This invention relates to a method of storing a product that contains a volatile component within a fluid storage reservoir formed with enclosing walls having a permeability that permits limited passage of the volatile component from the storage reservoir to the atmosphere, preferably with the method increasing the shelf life of the product stored.

The invention further relates to a fluid storage reservoir with a first container containing a fluid product to be dispensed including a volatile component and a second container containing a sacrifice material including the same volatile component with a n intermediate transfer wall shared by both the first container and the second container for transfer of the volatile component between the first container and the second container.

BACKGROUND OF THE INVENTION

Surface cleaners and hand sanitizers are known which include as an active ingredient ethanol typically with water in solutions containing 30 to 95% ethanol by weight and, more preferably, ethanol in the range of 40 to 90% and, more preferably, ethanol in the range of 60 to 80% and, most preferably, in the range of about 70%. The surface cleaners and hand sanitizers may include other components such as isopropyl alcohol, glycerine, carbomer, fragrances, aminomethyl propanol, propylene, glycol, isopropyl myristate and tocopheryl acetate. One known surface cleaner and hand sanitizer sold under the trademark PUREL™ and has as an active ingredient 70% weight/weight ethanol in an aqueous solution.

Ethanol kills organisms by denaturing their proteins and is effective against most bacterial fungus and many viruses. Ethanol is a volatile component. A hand sanitizer containing ethanol can be used by wetting one's hands with the hand sanitizer, briskly rubbing one's hands together until they become dry due to the evaporation of the hand sanitizer, notably, the ethanol at room temperatures.

It is well known to store ethanol based surface cleaners and hand sanitizers in bags, bottles and other receptacles. Ethanol based surface cleaners and hand sanitizers are known to be stored ready for use in various fluid storage reservoirs which may or may not incorporate a pump mechanism for dispensing the fluid. For example, product storage reservoirs are known that comprise a plastic bag or bottle and a pump assembly which together as a unit are removably insertable into a fluid dispenser for discharge of the cleaning fluid and subsequent removal and replacement as disclosed in U.S. Pat. No. 8,479,950 to Ophardt et al, issued Jul. 9, 2013 and U.S. Pat. No. 8,365,954 to Ophardt et al, issued Feb. 5, 2013. Various other product storage reservoirs are known including a collapsible bag formed from a thin flexible plastic material such as polyethylene containing the liquid to be dispensed.

Towards minimizing the cost of the fluid storage reservoirs, it is preferred to make the reservoirs from low cost plastic materials. Fluid storage reservoirs are often preferred to be collapsible by forming the reservoirs to have thin, flexible walls. Using reservoirs with thin walls has the advantage of minimizing the amount of material used to make a fluid storage reservoir. A disadvantage which arises from using with most plastics and notably inexpensive plastics such as polyethylene in forming a fluid storage reservoir is that the plastics are not impermeable to volatile compounds such as ethanol, rather the plastics have a permeability that lets volatile components such as ethanol pass through enclosing walls of the fluid storage reservoir. The disadvantage of the plastics having a permeability that lets volatile components pass through enclosing walls of a fluid storage reservoir increases as the thickness of the enclosing walls are reduced.

The inventors of the present application have appreciated the disadvantage that with the passage of time, volatile components such as ethanol, in stored products such as a hand sanitizer or surface cleaner, can permeate through the walls of the fluid storage reservoirs reducing both the volume of the stored product and the concentration of the volatile components from the stored product. The inventors of the present application have appreciated the disadvantage that with the passage of time, fluid reservoirs containing volatile components can have the volume of the stored product and the percentage of the volatile component in the stored product reduced such that the stored product becomes not acceptable for use or for sale. For example, a reduction in the product volume or a reduction in the concentration of the volatile component beyond predetermined levels may render the product inappropriate to sell or less than desirably effective. The present inventors have also appreciated that in the operation of facilities which fill product storage reservoirs with products containing volatile components such as ethanol based surface cleaners and hand sanitizers, it is often desired from a point of cost reduction to process a large batch of the product and to place the product of the batch within a large number of smaller fluid storage reservoirs, effectively at the same time. In the normal storage life of such smaller fluid storage reservoirs after becoming filled, they are warehoused, moved through distribution channels, and stored by the end user before being used by the end user. Many of these smaller fluid storage reservoirs are often stored for an extended period of time before they are used. Not infrequently, many of such filled smaller fluid storage reservoirs are stored for extended periods of time of many months or 1, 2 or more years before the product will be used.

SUMMARY OF THE INVENTION

To at least partially overcome some of these disadvantages of previously known devices, the present invention provides a method of increasing the shelf life of a product containing a volatile component by storing the product in an enclosed first container and providing a portion of an enclosing wall of the first container in contact with a sacrifice material containing the volatile component.

To at least partially overcome some of these disadvantages of previously known devices, the invention also provides a fluid storage receptacle comprising a first enclosed container containing a fluid product to be dispensed that includes a volatile component and a second enclosed container containing a sacrifice material that includes the volatile component with the first container and the second container sharing an intermediate transfer wall for transfer of the volatile component between the first container and the second container.

In one aspect, the present invention provides a fluid storage reservoir comprising:

a first container defining an enclosed interior within an enclosing wall member, the interior of the first container containing a product to be dispensed, the enclosing wall member of the first container including an intermediate transfer wall with an inner surface and an outer surface, the intermediate transfer wall defining at least in part the interior of the first container with the inner surface of the intermediate transfer wall in contact with the product, a second container defining an enclosed interior within an enclosing wall member, the interior of the second container containing a sacrifice material, the enclosing wall member of the second container including the intermediate transfer wall, the intermediate transfer wall defining at least in part the interior of the second container with the outer surface of the intermediate transfer wall in contact with the sacrifice material, the product comprising a fluid including a volatile component, the sacrifice material comprising a fluid including the volatile component, the intermediate transfer wall having a permeability between the first surface and the second surface selected from the following group:

(i) a permeability that permits passage of the volatile component through the intermediate transfer wall from the interior of the second container to the interior of the first container, and (ii) a permeability that permits passage of the volatile component through the intermediate transfer wall from the interior of the second container to the interior of the first container and from the interior of the first container to the interior of the second container, an escape transfer wall selected from the group consisting of:

(a) a first escape transfer portion of the enclosing wall member of the first container with an inner surface of the first escape transfer portion in contact with the product and an outer surface of the first escape transfer portion in contact with the atmosphere, the first escape transfer portion of the enclosing wall member of the first container having a permeability that permits passage of the volatile component through the enclosing wall member of the first container from the interior of the first container to the atmosphere, and (b) a second escape transfer portion of the enclosing wall member of the second container with an inner surface of the second escape transfer portion in contact with the sacrifice material and an outer surface of the second escape transfer portion in contact with the atmosphere, the escape transfer portion of the enclosing wall member of the second container having a permeability that permits passage of the volatile component through the enclosing wall member of the second container from the interior of the second container to the atmosphere.

In a $2^{nd}$ aspect, as in the $1^{st}$ aspect, the present invention provides a fluid storage reservoir wherein the intermediate transfer wall having a permeability that permits passage of the volatile component through the intermediate transfer wall between the interior of the first container and the interior of the second container.

In a $3^{rd}$ aspect, as in the $1^{st}$ or $2^{nd}$ aspect, the present invention provides a fluid storage reservoir wherein the product when placed in the first container having the volatile component in an initial product concentration, and the sacrifice fluid when placed in the second container having the volatile component in an initial sacrifice concentration equal to or greater than the initial product concentration.

In a $4^{th}$ aspect, as in the $3^{rd}$ aspect, the present invention provides a fluid storage reservoir wherein the initial sacrifice concentration is equal to or greater than the initial product concentration.

In a $5^{th}$ aspect, as in any one of the $1^{st}$ to $4^{th}$ aspects, the present invention provides a fluid storage reservoir container wherein the enclosing wall member of the first container includes a product outlet opening and a closure element closing the product outlet opening.

In a $6^{th}$ aspect, as in the $5^{th}$ aspect, the present invention provides a fluid storage reservoir container wherein the second container having an opening sealably engaged to the first container about the product outlet opening with the first container other than the product outlet opening and the closure element within the interior of the second container.

In a $7^{th}$ aspect, as in the $5^{th}$ or $6^{th}$ aspect, the present invention provides a fluid storage reservoir wherein the first container is disposed about an axis with the enclosing wall member of the first container including a circumferential side wall of the first container spaced radially from the axis, and closed at each axial end by first and second end walls of the first container, the first end wall of the first container carrying the product outlet opening, the second container is also disposed about the axis with a circumferential side wall of the second container spaced radially outwardly from the circumferential side wall of the first container and closed at each axial end by first and second end walls of the second container, an annular side space defined between the circumferential side wall of the first container and the circumferential side wall of the second container, the intermediate transfer wall including the circumferential side wall of the first container.

In an $8^{th}$ aspect, as in the $7^{th}$ aspect, the present invention provides a fluid storage reservoir wherein the escape transfer portion of the enclosing wall member of the second container including the circumferential side wall of the second container, and the escape transfer wall including the escape transfer portion of the enclosing wall member of the second container.

In a $9^{th}$ aspect, as in the $7^{th}$ aspect, the present invention provides a fluid storage reservoir wherein the first end wall of the second container is sealably engaged with the first container annularly about the outlet opening forming an annular first end space between the first end wall of the first container and the first end wall of the second container opening into the annular side space.

In a $10^{th}$ aspect, as in any one of the $6^{th}$ to $9^{th}$ aspects, the present invention provides a fluid storage reservoir wherein the second end wall of the second container is disposed axially outwardly from the second end wall of the first container.

In an $11^{th}$ aspect, as in the $10^{th}$ aspect, the present invention provides a fluid storage reservoir wherein the second end wall of the second container disposed axially spaced from the second end wall of the first container forming a second end space between the end wall of the first container and the end wall of the second container opening annularly into the annular side space.

In a 12th aspect, as in the 11th aspect, the present invention provides a fluid storage reservoir including a spacer located axially between the enclosing wall member of the first container and the enclosing wall member of the second container to space the outer surface of the enclosing wall member of the first container from the inner surface of the enclosing wall member of the second container maintaining a space there between.

In a 13th aspect, as in any one of the 6th to 12th aspects, the present invention provides a fluid storage reservoir wherein the first container having a rigidity that maintains the circumferential extent of the circumferential side wall of the first container yet permits axial movement of the second end wall of the first container towards the first end wall of first container to accommodate reductions in the volume of the product up to at least a maximum amount, preferably 5% by volume of the interior of the first container, a biasing mechanism urging the second end wall of the second container to move axially toward the first end wall of the first container forcing the sacrifice material into the annular space.

In a 14th aspect, as in the 13th aspect, the present invention provides a fluid storage reservoir wherein the second container having a rigidity that maintains the circumferential extent of the circumferential side wall of the second container yet permits axial movement of the second end wall of the second container towards the first end wall of second container.

In a 15th aspect, as in the 6th aspect, the present invention provides a fluid storage reservoir wherein the axis is vertical with the first end walls of the first container and the second container being vertically above the respective second end walls of the first container and the second container, the first container having a rigidity that maintains the circumferential extent of the side walls yet permits axial upward movement of the second end wall of first container to accommodate reductions in the volume of the product up to a maximum amount, preferably 5% by volume, a biasing mechanism urging the second end wall of the second container to move axially upwardly relative the first end wall of the second container forcing the fluid of the sacrifice material upwardly into the annular space and the first end space to fill the same while there is an adequate volume of the sacrifice material in the interior of the outer container.

In a 16th aspect, as in any one of the 1st to 15th aspects, the present invention provides a fluid storage reservoir wherein the volatile component is an alcohol and the product is a cleaning composition.

In a 17th aspect, as in the 16th aspect, the present invention provides a fluid storage reservoir wherein the product is an alcohol based surface disinfectant containing at least 40% of the alcohol as the volatile component, the sacrifice material comprises a solution of the alcohol having the alcohol in a percentage at least as great as the same percent of the alcohol in the alcohol based surface disinfectant.

In an 18th aspect, as in any one of the 1st to 17th aspects, the present invention provides a fluid storage reservoir including a mechanism for removing the sacrifice material from the second container.

In a 19th aspect, the present invention provides a method of increasing the shelf life of a product to be dispensed containing an initial concentration of a volatile component, the method comprising:

storing the product in an enclosed first container defining an enclosed interior within an enclosing wall member having a portion with a permeability that permits passage of the volatile component through the enclosing wall member between an inner surface of the enclosing wall member open into the interior and an opposed outer surface of the enclosing wall member, providing at least a transfer segment of the outer surface of the portion of the enclosing wall in contact with a sacrifice material containing the volatile component in an initial concentration greater than the volatile component occurs in atmosphere with the transfer segment having a permeability that permits passage of the volatile component through the transfer segment from the interior of the second container to the interior of the first container, providing an escape segment of the outer surface of the portion of the enclosing wall member of the first container with the inner surface in contact with the product with the escape segment having a permeability that permits passage of the volatile component through the enclosing wall member of the of the first container from the interior of the first container.

In a 20th aspect, as in the 19th aspect, the present invention provides a method wherein the transfer segment having a permeability that permits passage of the volatile component through the transfer wall both from the interior of the second container to the interior of the first container and from the interior of the first container to the interior of the second container.

In a 21st aspect, as in the 19th or 20th aspect, the present invention provides a method wherein the initial concentration the volatile component in the sacrifice material is greater than the initial concentration of the volatile component in the product.

In a 22nd aspect, as in the 19th, 20th or 21st aspects, the present invention provides a method wherein the volatile component is an alcohol and the product is a cleaning composition.

In a 23rd aspect, as in the 22nd aspect, the present invention provides a method wherein the product is an alcohol based surface disinfectant containing at least 40% of the alcohol as the volatile component, the sacrifice material comprises a solution of the alcohol having the alcohol in a percentage at least as great as the same percent of the alcohol in the alcohol based surface disinfectant.

In a 24th aspect, as in any one of the 19th to 23rd aspects, the present invention provides a method including providing a second container defining an enclosed interior within an enclosing wall member of the second container, providing the sacrifice material in the interior of the second container, providing the transfer segment to define at least in part the interior of the second container with the outer surface of the transfer segment in contact with the sacrifice material and to define at least in part the interior of the first container with the inner surface of the transfer segment in contact with the product, providing an escape portion selected from the group consisting of:

(a) an escape portion of the enclosing wall member of the first container with the inner surface in contact with the product and the outer surface in contact with the atmosphere with the escape portion of the enclosing wall member of the first container having a permeability that permits passage of the volatile component through the enclosing wall members of the first container from the interior of the first container to the atmosphere, and (b) an escape portion of the enclosing wall member of the second container with the inner surface in contact with the product and the outer surface in contact with the atmosphere with the escape portions of the enclosing wall members of the second container having a permeability that permits passage of the volatile component through the enclosing wall members of the second container from the interior of the second container to the atmosphere.

In a 25$^{th}$ aspect, as in the 24$^{th}$ aspect, the present invention provides a method wherein selecting the initial concentration of the volatile component in the fluid product and the initial concentration of the volatile component in the sacrifice material such that from an initial fill point of time when the first container is filled with the fluid product and the second container is filled with the scavenger material, a shelf life time that the fluid product maintains a concentration in excess of a minimum concentration of the volatile component is increased to a predetermined time having the regard to factors including:

i) the relative surface areas of the transfer segment and the escape segment;

ii) the relative permeability of the volatile component through the transfer segment and the escape segment; and iii) the difference between the initial concentration of the volatile component in the fluid product and the initial concentration of the volatile component in the sacrifice material.

BRIEF DESCRIPTION OF THE DRAWINGS

Further aspects and advantages of the present invention will become apparent from the following description taken together with the accompanying drawings in which.

DETAILED DESCRIPTION OF THE DRAWINGS

Reference is made to FIGS. 1 to 4 illustrating of a first embodiment of a fluid storage reservoir 10 in accordance with the present invention.

Figure 3:
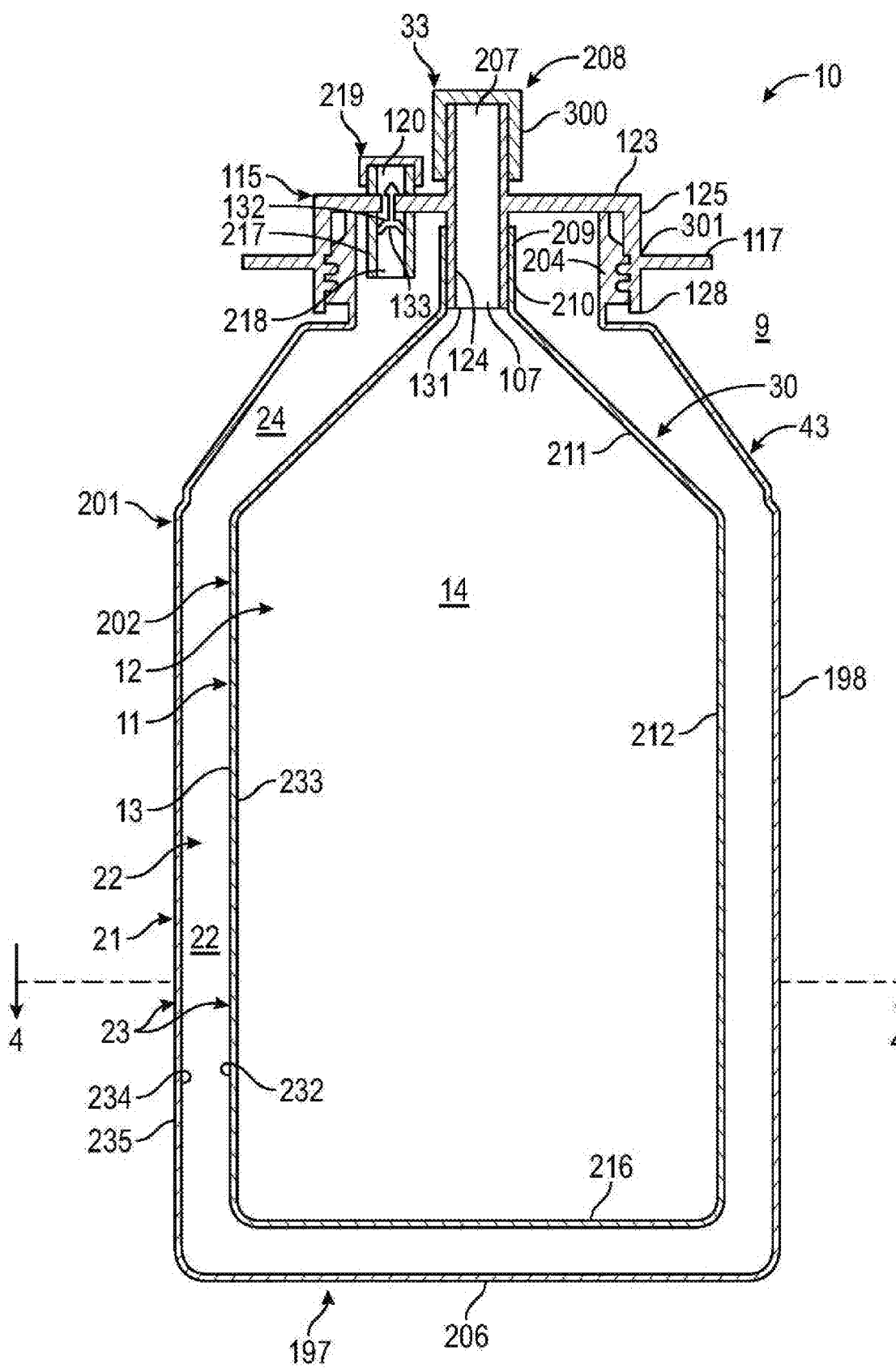
FIG. 3 is a cross-sectional front view of the cartridge shown in FIG. 1.

As best seen in FIG. 3, the fluid storage reservoir 10 is formed from five components, namely a collapsible outer bottle 201, a collapsible inner bag 202, a cap body 115, a first closure cap 208 and a second closure cap 219.

Figure 1:
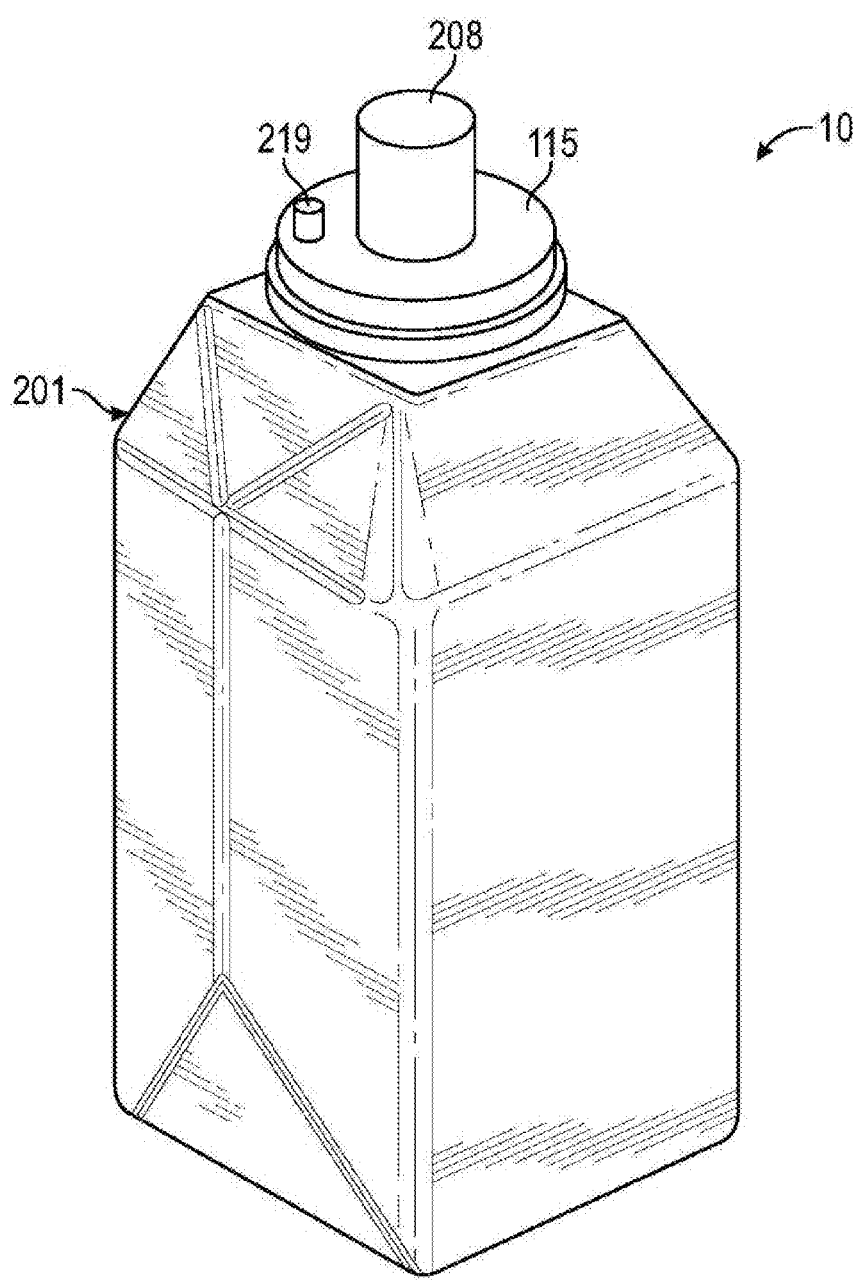
FIG. 1 is a pictorial view of a first embodiment of a fluid storage reservoir in accordance with the present invention.
Figure 2:
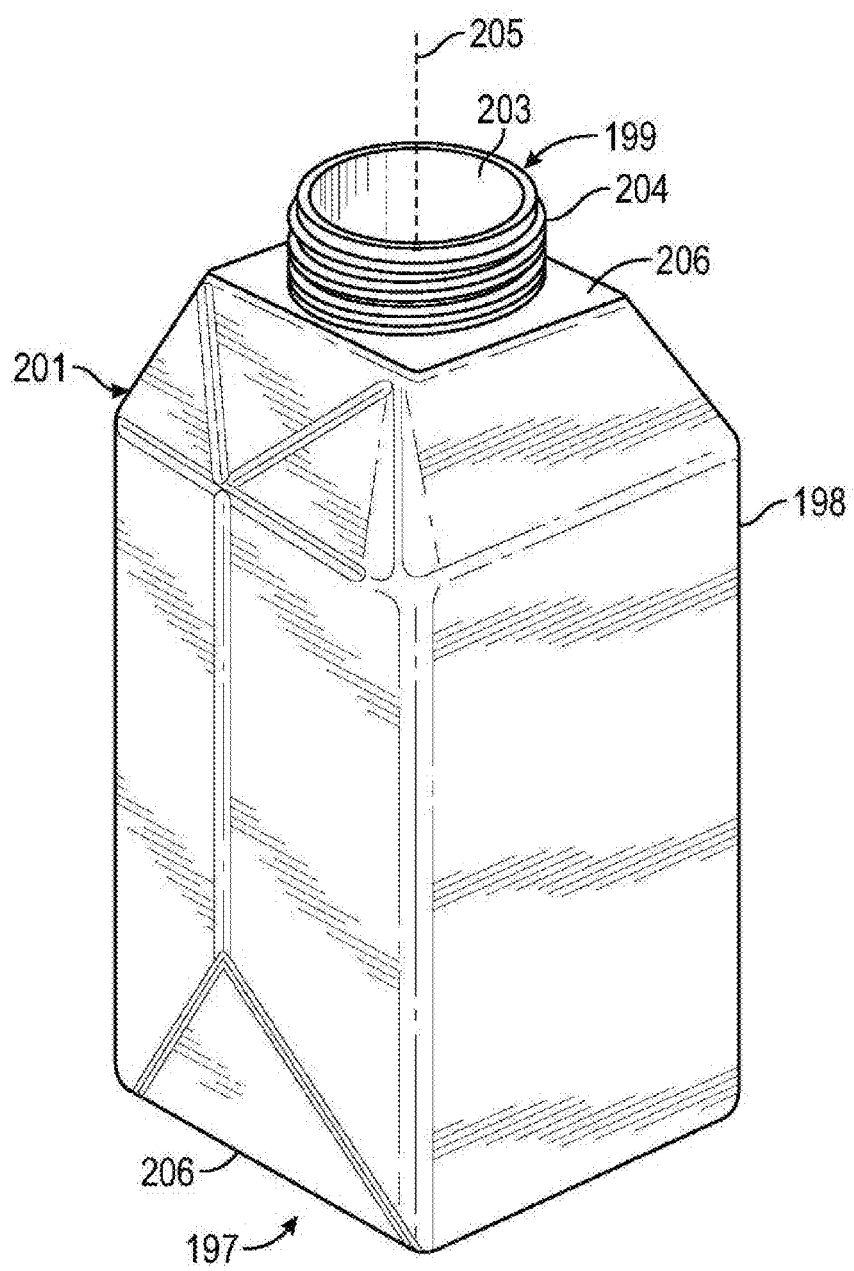
FIG. 2 is a pictorial view of an outer bottle of the fluid storage reservoir of FIG. 1.

As best seen in FIG. 2, the bottle 201 is closed but for an opening 203 provided at a first end 199 of the bottle 201. The opening 203 is provided at the end of an externally threaded cylindrical neck 204 disposed about a longitudinal center axis 205. The neck 204 extends upwardly from a shoulder surface 206 at the first end 199 of the bottle 201 and merges into the circumferential side walls 198 which are closed at a second end 197 of the bottle 201 by a second end wall 206.

The cap body 115 has an end wall 123 supporting both a cylindrical inner tube 124 and cylindrical outer tube 125 coaxial about the common center axis 126. The cylindrical inner tube 124 extends between an open first end 207 and an open second end 107. The inner tube 124 has an opening 131 at a second end 107 and an opening at a first end 207. The exterior of the inner tube 124 about the first end 207 carries external threads 300. The first closure cap 208 is threadably received on the first end 207 of the inner tube 124 to removably seal the first end 207.

The cylindrical outer tube 125 extends from the end wall 123 to an open inner end 128. An optional annular engagement flange 117 extends radially outwardly from the cylindrical outer tube 125. The outer tube 125 is provided with internal threads 301 adapted to removably engage in a threaded manner with the external threads on the neck 204 of the bottle 201.

The bag 202 is closed but for being open at an opening 209 at the end of a cylindrical neck 210 of the bag 202 merging into a shoulder wall 211 and hence into a circumferential wall 212 which merges into a second end wall 216 of the bag 202. The neck 210 of the bag 202 is sealably engaged to a radially outer surface of the inner tube 124 about the open first end 107, preferably by heat welding, to form a fluid impermeable seal therebetween.

The end wall 123 of the cap body 115 includes a cylindrical fill tube 217 disposed parallel to the axis 126 but located between the inner tube 124 and the outer tube 125. The fill tube 217 extends from the end wall 123 between an open first end 120 and an open second end 218. The fill tube 217 carries external threads 302 about the first end to threadably removably sealably receive the second closure cap 219 and close the fill tube 217 to fluid flow.

A first enclosed container 11 is defined by the inner bag 202, the inner tube 124 and the first closure cap 208. This first container 11 has an enclosed interior 12 defined within the bag 202, the inner tube 124 and the first closure cap 208. The first container 11 may be characterized as having an enclosing wall member 13 formed by the wall of the bag 202, the wall of the inner tube 124 and the wall of the first closure cap 208.

The enclosed interior of the first container 11 is defined within the enclosing wall member 13 by the inner surface 233 of the wall of the bag 202, the radially inner surfaces of the inner tube 124 and inner surfaces of the first closure cap 208.

A second container 21 is defined by the bottle 201, the bag 203, the cap body 115 and the second closure cap 219. The second container 21 has an enclosed interior 22 defined between the bottle 201, the bag 203, the cap body 115 and the second closure cap 219. The second container 21 may be characterized as having an enclosing wall member 23 comprising the wall of the bottle 201, the wall of the outer tube 125, the end wall 123 of the cap body 115 between the outer tube 125 and the inner tube 124, the wall of the inner tube 124 and the wall of the bag 202. This enclosing wall member 23 defines the second container 21 to have the enclosed interior 22.

The enclosed interior 22 of the second container 21 is defined within the inner surface 234 of the wall of the bottle 201, an outer surface 232 of the wall of the bag 201, a radially inner surface of the outer tube 125, an axially inner surface of the end wall 23 and a radially outer surface of the inner tube 124 inwardly from the end wall 123.

As schematically marked on FIG. 3, the enclosed interior 12 of the first container 11 is filled by a fluid product 14 and the enclosed interior 22 of the second container 21 filled by a sacrifice fluid 24. The fluid product 14 contains a volatile component such as, for example, ethanol in an initial product concentration. The sacrifice fluid 24 comprises a fluid also including the same volatile component.

In one preferred manner of assembly and filling, the bag 202 preferably while empty and collapsed, is fixedly sealably engaged to the inner tube 124 about the first end 107. The bag 202, preferably in a collapsed condition, is fed into the bottle 201 through the opening 202 and the cap body 115 is then threadably sealably engaged on the neck 204 of the bottle 201. With both the first closure cap 208 and the second closure cap 219 removed, the first container 11 is filled with the fluid product 14 via the opening 202 and the first closure cap 208 is then applied preferably resulting with the first container 11 being completely filled with the fluid product. After filling the first container 11 with a predetermined volume of the product 14, a sacrifice fluid 24 is passed through the fill tube 217 into the second container 21 preferably filling the second container 21 such that the second container 21 is filled in its entirety by the bag 202 and the sacrifice fluid without any atmospheric air within the first container 11, although this is not necessary. The second closure cap 219 is then secured to seal the fill tube 217.

The bag 202, as seen in FIG. 3, has its walls formed from a thin flexible plastic material having the inner surface 233 and the outer surface 232. The bottle 201 preferably has its walls formed from relatively thin plastic material having the inner surface 234 and an outer surface 235. In accordance with the first embodiment of FIGS. 1 to 4, each of the bottle 201 and the bag 202 is collapsible. As the volatile component, such as ethanol, permeates from the fluid storage reservoir 10, the bottle 201 will collapse and, similarly, the bag 202 will collapse.

The fluid storage reservoir 10 is preferably adapted to be self-supporting and its end wall 206 of this will be a function of the nature of the bottle 201.

To dispense the product 14 from the fluid storage reservoir 10, the first closure cap 208 may be removed and the product 14 drawn or poured out the outer end 207 of the inner tube. For example, if fluid is drawn by a pump from the outer end 207 of the inner cap without permitting air to flow into the first container 11, then with the dispensing of the product 14, the bag 202 will collapse and with the collapse, there is a reduction in volume of the first container 11 and a reduction in the volume of the second container 21 such that the collapsible bottle 201 will also collapse.

Figure 4:
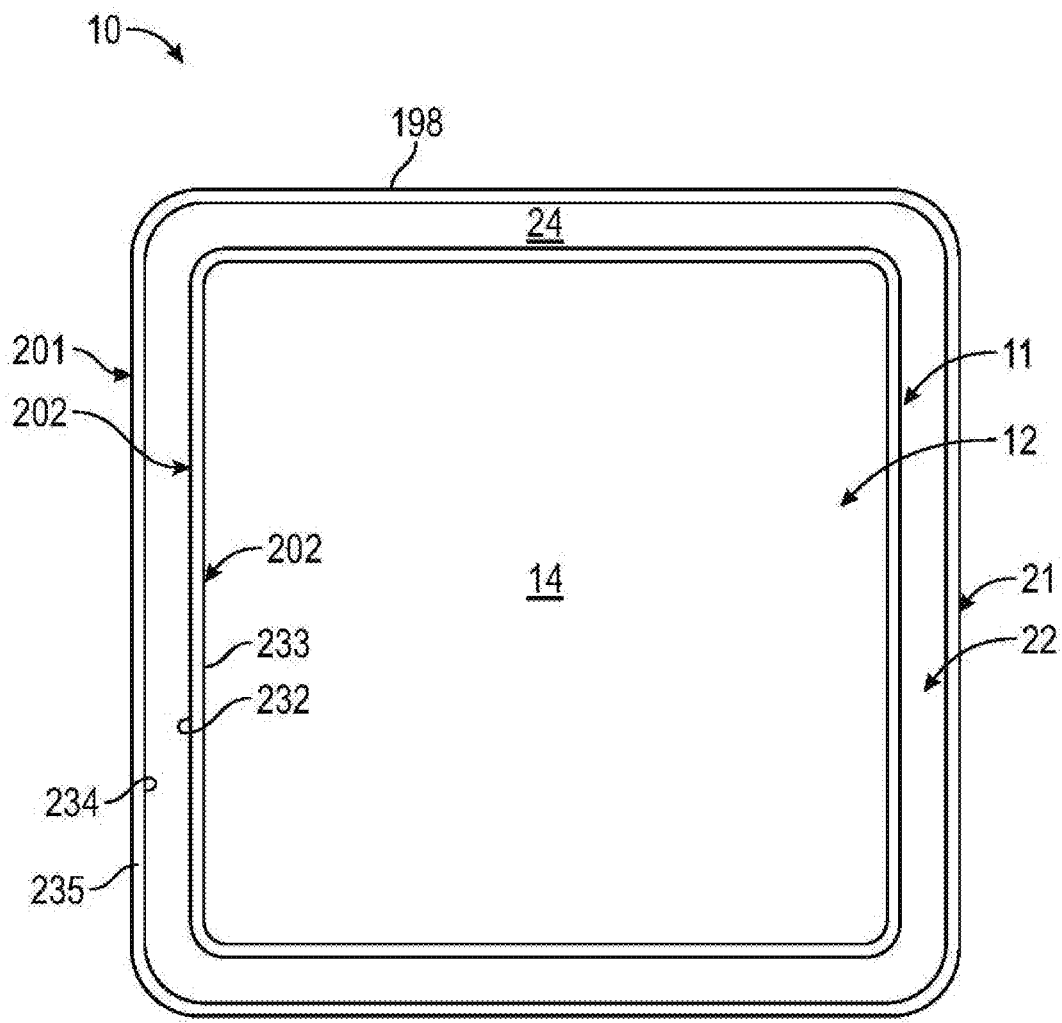
FIG. 4 is a cross-sectional plan view of the cartridge in FIG. 1 along section line 4-4' on FIG. 3.

As can be seen in FIGS. 3 and 4, the bag 202 is selected to have a shape, size and configuration such that when the bag 202 is filled with the product 14, that the bag 202 adopts a configuration which provides for a space between the outer surface 232 of the bag 202 and the inner surface 233 of the bottle 201. This space 236 comprises part of the second container 21 that is filled with the sacrifice fluid 24.

FIG. 3 shows the fluid storage reservoir 10 as surrounded by the atmosphere 9 comprising atmospheric air. As seen on FIG. 3, the enclosing wall member 13 of the first container 11 has portions which are open to the surrounding atmosphere 9 now referred to a first escape transfer portion 33 of the enclosing wall member 13 of the first container 11 and comprising the portion of the enclosing wall member 13 defined by the inner tube 124 outward of the end wall 123 and the first closure cap 208. Over this first escape transfer portion 33, an inner surface is in contact with the fluid product 14 in the interior 12 of the first container 11 and an outer surface is in contact with the atmosphere 9. This first escape transfer portion 33 of the enclosing wall member 13 may have at least some segments with a permeability that permits limited passage of a volatile component in the product 14 through the enclosing wall member 13 from the interior 12 of the first container 11 to the atmosphere 9.

In the first embodiment as seen in FIG. 3, the enclosing wall member 13 of the first container 11 other than the first escape transfer portion 33 comprises an intermediate transfer wall 30 with a first surface in contact with the fluid product 14 within the interior 12 of the first container 11 and with a second surface of the intermediate transfer wall 30 in contact with the sacrifice fluid 24 within the interior 22 of the second container. As seen in FIG. 3, the intermediate transfer wall 30 comprises the entirety of the wall of the bag 202 as well as portions of the inner tube 124 inwardly of the end wall 123. The intermediate transfer wall 30 will have at least some segments with a permeability that permits passage of the volatile component through the intermediate transfer wall 30 from the interior 22 of the second container 21 to the interior 12 of the first container 11 and passage of the volatile component through the intermediate transfer wall 30 from the interior 12 of the first container 11 to the interior 22 of the second container 21.

In the first embodiment, other than the portion of the enclosing wall member 23 of the second container 21 that comprises the intermediate transfer wall 30, the enclosing wall member 23 comprises a second escape transfer portion 43 which has an inner surface in contact with the sacrifice fluid 24 in the interior 22 of the second container and an outer surface in contact with the atmosphere 9. The second escape transfer portion 43 of the enclosing wall member 23 of the second container 21 has at least some segments with a permeability that permits passage of the volatile component through the enclosing wall member 23 of the second container from the interior 22 of the second container 21 to the atmosphere 9. The second escape transfer portion 43 of the enclosing wall member 23 of the second container 21 comprises the entirety of the wall of the bottle 201 together with the wall of the outer tube 125 and a portion of the end wall 123 between the outer tube 125 and the inner tube 124.

With the first container 11 filled with the product 14 and the second container 21 filled with the sacrifice fluid 24 and the fluid storage reservoir exposed to the atmosphere 9 as in FIG. 3, there will arise propensities for:

1. escape of the volatile component from the first container 11 to the atmosphere 9 through the first escape transfer portion 33;
2. escape of the volatile component from the second container 21 to the atmosphere 9 through the second escape transfer portion 43; and
3. transfer of the volatile component through the intermediate transfer wall 30 between the first container 11 and the second container 21.

The rate of transfer of the volatile component through any segment of the enclosing wall member 13 of the first container 11 or the enclosing wall member 23 of the second container 21 may be calculated as a function of: (a) permeability of the volatile component through that segment of the enclosing wall member, (b) the area of that segment of the enclosing wall member, (c) the difference between the concentrations of the volatile component in contact with opposing sides of the enclosing wall member, and (d) the temperature. Based on the knowledge of each of the rate of transfer of the volatile component through each segment of the enclosing wall members, the volume of each of the product 14 and the sacrifice fluid 24 at an initial time, the concentration of the volatile component in the product 14 and in the sacrifice fluid 24 at the initial time, the permeability of the volatile component through each segments of the enclosing walls of the first container 11 and the second container 21, the area of each segment, and the temperature with time, then the concentration of the volatile component in each of the product 14 and the sacrifice fluid 24 can be calculated over time, as can the volume of the product 14 with time.

By a trial and error calculation basis, the shelf life of the product 14 in a fluid storage reservoir 10 in accordance with the present invention may be established representing the time from initial filling that the volume of the product or the concentration of a volatile component in the product will be less than or greater than predetermined values or within a desired range of values. The fluid storage reservoir 10 may be selected as to the materials of its components, the relative proportions of the components, the nature of the product and the sacrifice material including particularly their concentration of any volatile components so as to provide a desired shelf life for the product 14 in a selected fluid storage reservoir 10.

In the preferred embodiment, each of the components forming the fluid storage reservoir 10 are preferably formed from plastic material, preferably ethylene. The cap body 115, the first closure cap 208 and second closure cap 219 may be injection molded as from various different plastics and may be formed from other materials. The outer bottle 201 is preferably formed from a plastic material, preferably polyethylene as by injection molding or blow molding. The inner bag 202 is preferably formed from plastic, preferably ethylene, preferably with the inner bag 202 to have its walls formed of a thin flexible sheet-like material such that the inner bag 202 is readily collapsible as the volume within the inner container 11 decreases. The outer bottle 201 is preferably collapsible in the sense that as the volume of the first container 11 and/or the second container 21 reduces, the walls of the bottle 201 will readily permit the bottle 201 to collapse to assume a corresponding reduced volume.

FIG. 3 illustrates an optional one-way valve 132 is provided within the fill tube 217 to permit fluid flow axially pass the one-way valve 132 into the second container 21 but to prevent fluid flow from the second container 21 to the atmosphere. In this regard, the one-way valve 132 includes a member across the fill tube 217 with a central opening and at least at one passage opening. A resilient valve 133 is supported in the fill tube 217 by a central stem received in the central opening so as to locate a cylindrical sealing disc within the fill tube 217. A radially outer edge of the sealing disc is biased into the internal side wall of the fill tube 217 to prevent fluid flow from the interior 12 of the second container 21 therepast to the atmosphere yet permit fluid flow from the past disc from the atmosphere to the second container when the second closure cap 219 is removed.

Provision of the optional one-way valve 132 can be advantageous after storage when product 14 may be desired to be pumped from the first container 11 so as to facilitate reduction of the volume of the first container 11 by the collapse of the collapsible bag 202 yet without requiring the outer bottle 201 to completely collapse. The outer bottle 201 may be formed to be readily collapsible to an extent that accommodates the loss of volume of the second container 21 and the first container 11 during storage of the fluid storage reservoir 10 in its desired shelf life. For example, the outer bottle 201 may have walls with a resiliency that readily accommodates collapse of up to 5, 10 or 20% of the volume of the second container 21. After storage, when the fluid storage reservoir 10 is to be used and the product 14 is to be drawn from the first container 11, the second closure cap 219 can be removed. With discharge of the product 14 from the first container 11, a vacuum will be created within the second container 21 which vacuum will give rise to the bottle 201 collapsing until such time as the vacuum reaches a threshold vacuum which causes the one-way valve 132 to permit atmospheric air to be drawn into the second container 21 at least partially relieving the vacuum. With the provision of the one-way valve 132, the bottle 201 may be provided to be collapsible while the second closure cap 219 is in place merely to an extent as may be advantageous to accommodate the loss of volumes of the first container 11 and the second container 21 due to the escape of the volatile component during the shelf life. During dispensing of the product 14 from the first container, the one-way valve 132 can accommodate the bottle 201 being unable to further collapse.

In the first embodiment, the five components, namely, the bottle 201, the bag 202, the cap body 115, the first closure cap 208 and the second closure cap 219 can be formed from plastic materials that have at least some limited permeability for the volatile component. However, each of these components or at least portions of them may be formed so that they have little or no permeability. For example, the first closure cap 208, the second closure cap 209 and/or the cap body 115 may be formed to have no permeability to the volatile component or at least reduced permeability particularly insofar as they may be provided to have relatively thick wall structures or may be formed from materials with nor or low permeability. Generally, the permeability through a wall will be increased as the thickness of the wall increases. In respect of the bag 202, the bag 202 is preferably formed from a relatively uniform thin walled flexible plastic material such as polyethylene which will be expected to have a relatively consistent permeability to the volatile component over its entire surface area. Of course, it is possible that the bag 202 may be selected to have different segments of increased thickness which might change the permeability over those sections. The bottle 201 preferably is formed with a relatively constant thickness wall although the thickness of the wall and therefore the permeability through segments of the wall may be different over the different segments of the bottle 201. Similarly, the permeability through the neck of the bottle which is of increased thickness would be expected to be decreased compared to the inner wall of the bottle. In the preferred embodiment, the wall of the bag 202 has a permeability that permits passage of the volatile component in both directions through the wall of the bag and the wall of the bottle 201 also has a permeability that permits passage of the volatile component in both directions through the wall of the bottle 201.

The fluid product 14 when placed in the first container 11 has the volatile component in an initial product concentration. The sacrifice fluid 24 when placed in the second container 21 has the volatile component in an initial sacrifice concentration. The initial sacrifice concentration may be less than equal to or greater than the initial product concentration. Preferably, the initial sacrifice concentration is at least equal to or greater than the initial product concentration and, most preferably, the initial sacrifice concentration is greater than the initial product concentration.

Compared to the fluid storage reservoir 10 in accordance with the first embodiment illustrated in FIGS. 1-4, a hypothetical comparative reservoir may be envisioned identical to that illustrated in FIG. 3, however, with the bottle 201 removed and the first container 11 completely filled with a product 14 containing a hand sanitizing product of 70% ethanol by weight as the volatile component. In such a comparative reservoir, the rate of transfer of ethanol within the bottle 201 to the atmosphere 9 will be a function of the ethanol concentration in the first container 11 compared to the ethanol concentration in the atmosphere which is zero. The ethanol concentration within the first container 11 in this comparative reservoir will decrease with time. In contrast with this comparative reservoir, the fluid storage reservoir 10 in FIG. 11 may be considered in a first example in which the first container 11 is filled with the same hand sanitizing fluid containing 70% ethanol by weight and the second container is filled with an aqueous solution of water and ethanol with 70% ethanol by weight. The mere fact that the ethanol in the first container 11 to be transferred to the atmosphere must permeate both through the enclosing wall member 13 of the first container 11 into the second container 21 and then through the enclosing wall member 23 of the second container 21 will in itself increase the length of time that it would take for the ethanol concentration within the first container 11 to reach a pre-determined lower concentration such as 60% as compared to the time this would take in the comparative reservoir. However, in the first example, initially a rate of transfer of ethanol from the first container 11 to the second container 21 will be zero since the ethanol concentrations in the first container 11 and the second container 21 are then equal. As the ethanol concentration in the second container 21 reduces, then the rate of transfer of the ethanol from the first container 11 to the second container 21 will increase from zero. However, until such time as the ethanol concentration in the second container 21 reaches hypothetically zero, then the rate of transfer of the ethanol from the first container 11 to the second container 21 will be reduced compared to the comparative reservoir in which the enclosing wall member 13 of the first container 11 is always open to the atmosphere having an ethanol concentration of zero.

In the first embodiment of FIGS. 1-4, as a second example, the product 14 is the same as in the first example with 70% ethanol and the aqueous sacrifice fluid 24 is a solution of water and ethanol having 90% ethanol. In this second example, initially after filling, there will be a transfer of ethanol from inside the second container 21 to the atmosphere and, as well, a transfer of ethanol from the second container 21 into the first container 11. The ethanol concentration in the first container 11 will increase until it becomes equal to the decreasing level of ethanol in the second container 21. Thereafter, the relative concentrations in the first container 11 and the second container 21 will decrease as in the first example.

In a third example, the product 14 is the same as the first two examples with 70% ethanol and the sacrifice fluid 24 is a solution of water and ethanol having 40% ethanol. In this third example, compared to the comparative reservoir, from initial filling, there will be transfer of ethanol both from the second container 21 to the atmosphere 9 and from the first container 11 to the second container 21, however, the rate of transfer from the first container 11 to the second container 21 will be less than the rate of transfer from the first container 11 to the atmosphere 9 at comparable times in the comparative reservoir.

In accordance with the present invention, by selecting suitable initial concentrations of ethanol in the sacrifice fluid 24, the fluid storage reservoir 10 can be configured to provide the product 14 with an ethanol concentration between some desired acceptable range such as between 75% and 60% during selected periods of time following the initial fill time, for example, from the $4^{th}$ month after filling to the $8^{th}$ month after filling, or to have a shelf life during which the ethanol concentration in the product does not drop below a desired limit, for example, 60%.

In accordance with a method of the present invention, a large batch of product 14 may be prepared, for example, of 10,000 liters having a consistent composition with 70% ethanol. The product 14 may be filled into the 10,000 separate fluid storage reservoirs 10 each having a volume of 1 liter of the product in the first container. 5,000 of the fluid storage reservoirs 10 may have the second container filled with the sacrifice material having 70% ethanol; 3,000 of the fluid storage reservoirs 10 may be filled with sacrifice material 24 having 80% ethanol and 2,000 of the fluid storage reservoirs 10 may be filled with sacrifice material containing 90% ethanol. Each of the 10,000 reservoirs will be marked with a marking indicating a period of time for best use calculated when the ethanol in the first container is in a desired range of 70% to 60%. By varying the ethanol concentration in the sacrifice fluid 24, the periods of times from initial filling when the product is best for use can be varied. As another variation, rather than vary the ethanol concentration of the sacrifice fluid 24, the relative volume of the sacrifice fluid 24 can be varied such that with the provision of a larger volume of sacrifice fluid 24 in one reservoir 10 compared to another reservoir, the length of time after initial filling that reservoir 10 will have a period for best use which will increase. Similarly, both the ethanol concentration and the volume of the sacrifice fluid 24 may be varied to change the period for best use.

The desired shelf life of product 14 may be selected, for example, to be a period of time such as two years during which the ethanol concentration in the product will not drop below a predetermined minimum, for example, 60% by weight and with, for example, at the end of the two years, the ethanol concentration dropping from 60% to just below 60%.

Figure 5:
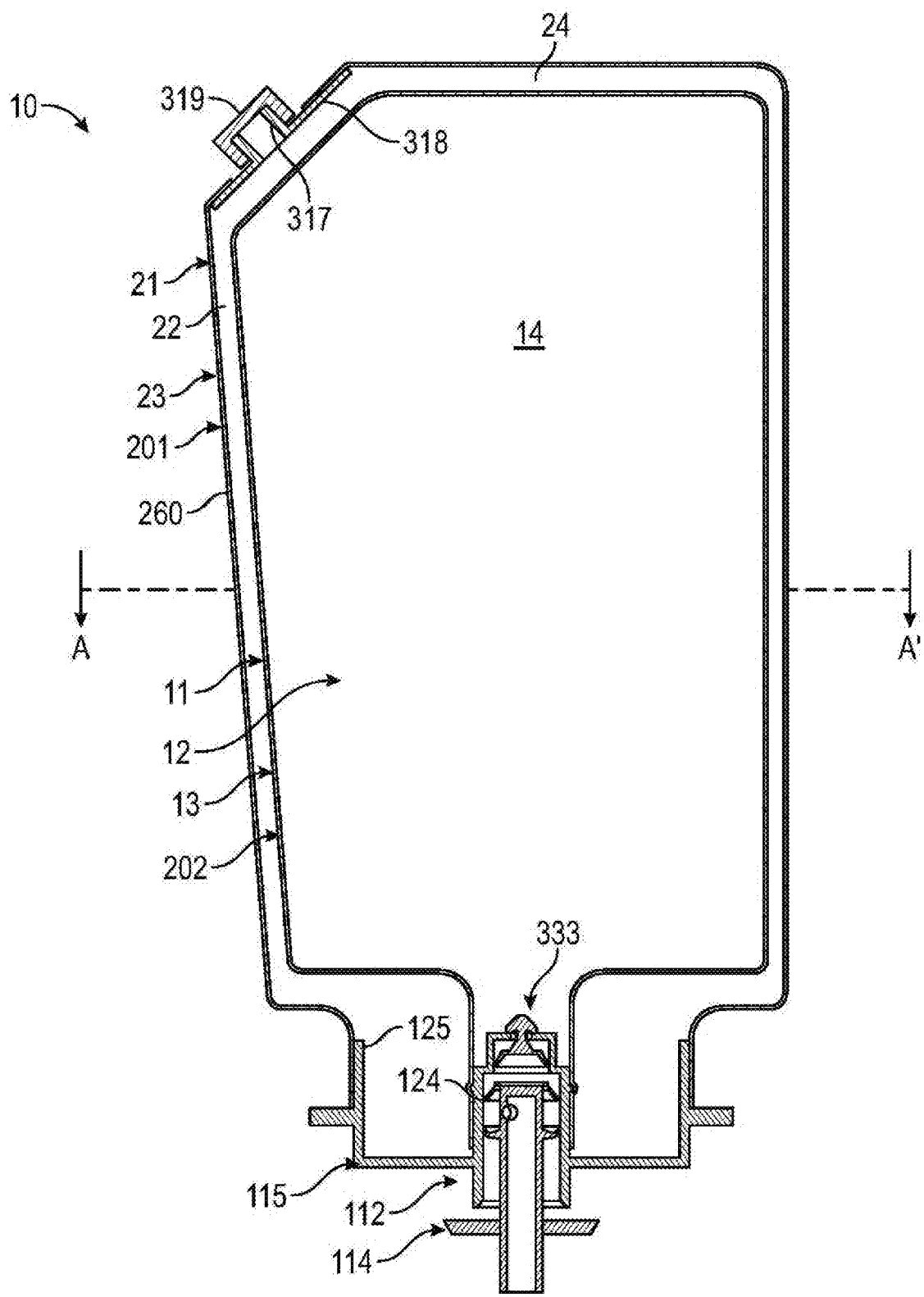
FIG. 5 is a cross-sectional front view of a fluid storage reservoir in accordance with a second embodiment of the present invention.
Figure 6:
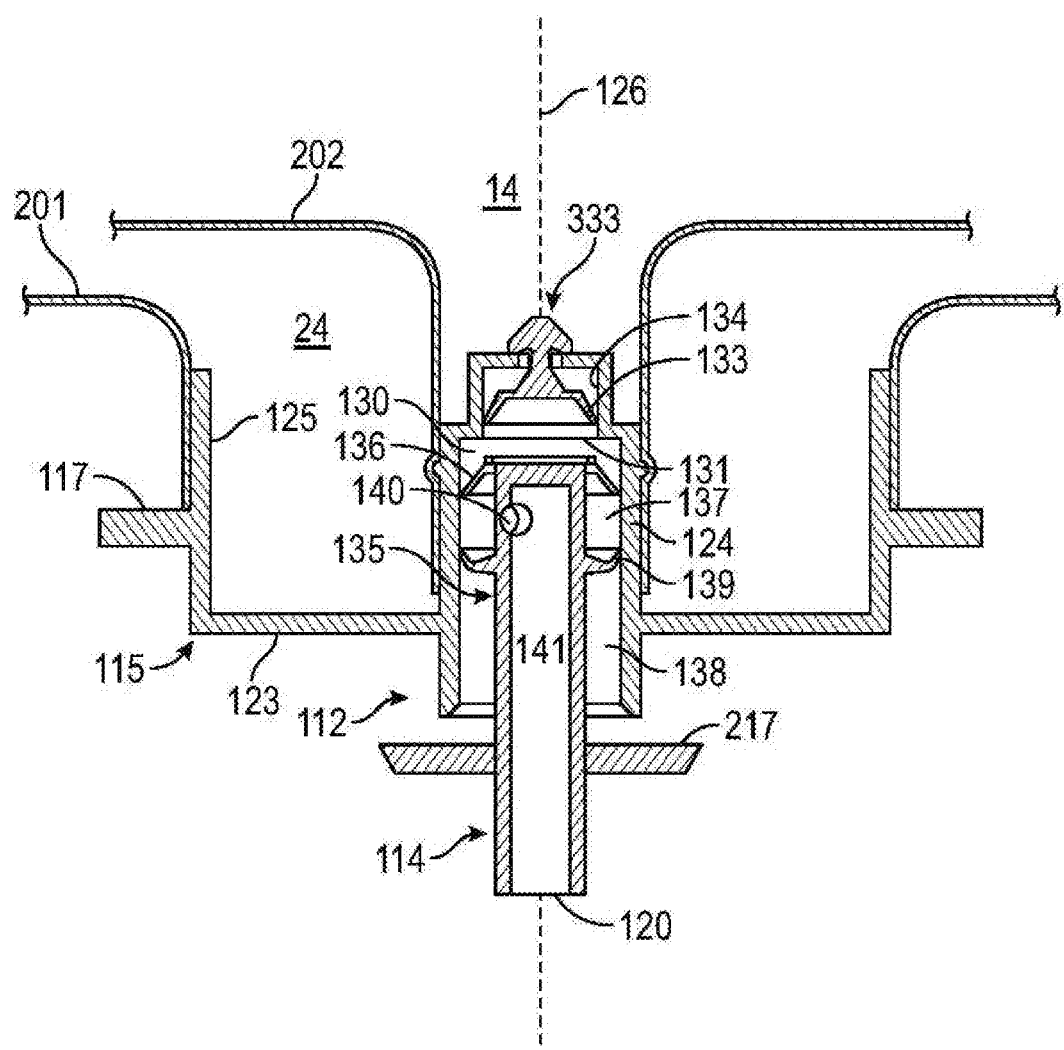
FIG. 6 is an enlarged portion of the fluid storage reservoir shown in FIG. 5.

Reference is made to FIGS. 5 and 6 which illustrate a second embodiment of a fluid storage reservoir 10 in accordance with the present invention. Throughout the Figures, similar reference numerals are used to refer to similar elements.

The second embodiment of a fluid storage reservoir 10 of FIGS. 5 and 6 has many similarities to the first embodiment shown in FIG. 3, however, with a number of differences. A first difference is that the bottle 201 is replaced by a fully collapsible outer bag 201 having a bag wall 260 formed from a thin flexible material and with an opening of the outer bag 201 sealed to a radially outer surface of the outer tube 125 of the cap body 115 as by heat welding rather than by a threaded connection as was the case with the bottle 201 in the first embodiment. A second difference is that the fill tube 217 and its second closure cap 219 has been eliminated. A third difference is that the outer bag 210 is provided proximate its second end wall 206 remote from the cap body 115 with a fill tube 317 closable by a threaded second closure cap 319 with the fill tube 317 having an annular flange 318 heat sealed to the wall 260 of the outer bag 201 annularly about an opening through the wall of the outer bag 201. A fourth difference is that the first closure cap 208 has been eliminated and replaced by both a piston-forming element 114 coaxially received within the cylindrical inner tube 124 and a one-way inlet valve 332 which form with the inner tube 124 a piston pump assembly 112.

As in the first embodiment in FIGS. 5 and 6, the first container 11 is defined with an enclosed interior 12 within an enclosing wall member 13 comprising the inner bag 202, portions of the inner tube 124 and the one-way valve 333. A second container 21 having an enclosed interior 22 is defined within an enclosing wall member 23 comprising the outer bag 201 together with portions of the cap body 115 and portions of the inner bag 202. The first container 11 is filled with the fluid product 14 to be dispensed containing a volatile component. The second container 21 is filled with the sacrifice fluid 24 containing the same volatile component. In the embodiment of FIGS. 5 and 6, in use to dispense the product 14 with operation of the pump assembly 112 to draw the fluid product 14 from the first container 11, the inner bag 202 collapses and with collapse of the inner bag 202, the outer bag 201 also collapses. In the embodiment of FIGS. 5 and 6, the walls of outer bag 201 and the inner bag 202 are formed from flexible thin material such as preferably polyethylene which readily collapses when the product 14 is drawn from the inner bag 202.

Figure 7:
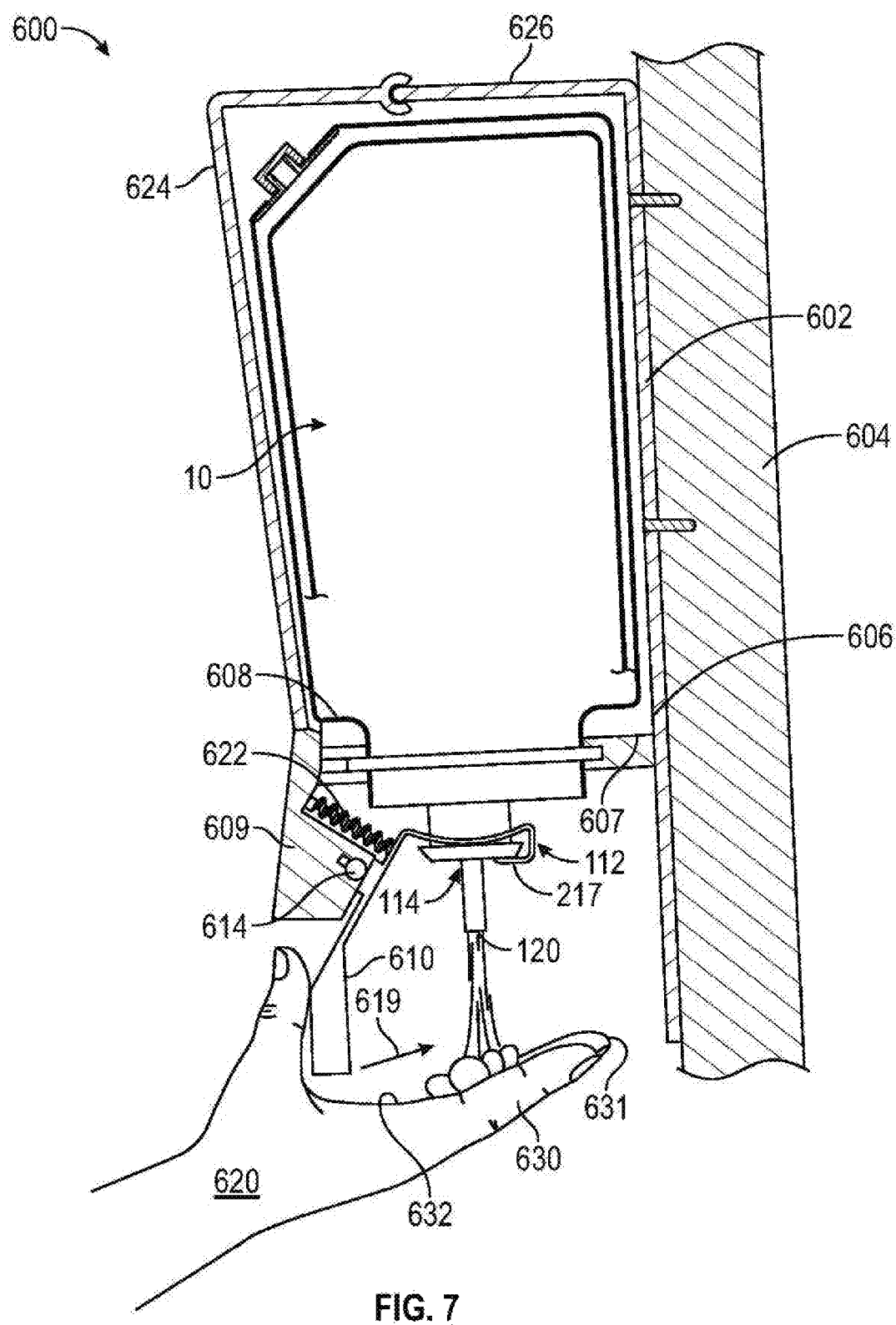
FIG. 7 is a partially cutaway schematic side view of a hand cleaner dispenser including the fluid storage reservoir of FIGS. 5 and 6.

Reference is made to FIG. 7 which shows the fluid storage reservoir 10 of the second embodiment of FIGS. 5 and 6 received within a manually operated hand cleaner foam dispenser 600. The dispenser 600 is adapted to removably receive the fluid storage reservoir 10. The dispenser 600 is shown in side cross-section other than an activating lever 610 which is schematically shown in side view and not cross-sectioned. The fluid storage reservoir 10 is shown with a lower portion in side view and an upper portion in cross-section. A user's hand 620 is shown in side view and not in cross-section.

The pump assembly 112 includes the piston-forming element 114 and the inner tube 124 of the cap body 115. The piston-forming element 114 carries a discharge outlet 120 to discharge the fluid product 14 as a liquid stream onto the upturned palm 632 and/or fingers 630 of the user's hand 620.

In FIG. 7, the dispenser 600 includes a back plate 602 as for mounting of the dispenser 600 to a building wall 604. A support plate 606 extends forwardly from the back plate 604 to support and receive the fluid storage reservoir 10. The support plate 606 has a rear portion 607, two side arms 608 (only one of which is seen) and a forward portion 609. The side arms 608 extend forwardly from the rear portion 607 to support the forward portion 609 forming a lower front wall of the dispenser 600. The support plate 606 has an opening extending downwardly therethrough defined between the side arms 608 and between the forward portion 609 and the rear portion 607 via which opening 612 the fluid storage reservoir 10 may be inserted downwardly and then slid rearwardly for secure engagement of the fluid storage reservoir 10 on the support plate 606 with an annular engagement flange 117 on the cap body 115 of the pump assembly 112 engaged within complementary slots 607 in the support plate 606 that open into the opening 612.

The activating lever 610 is journaled to the forward portion 609 for pivoting about a horizontal axis 614. An upper end of the lever 610 carries a hook 616 to engage an annular engagement flange 217 on the piston-forming element 114 of the pump assembly 112 and couple the lever 610 to the piston-forming element 114 such that by movement of a lower handle end of the lever 610 in the direction indicated by the arrow 619 manually by the hand 620 of a user slides the piston-forming element 114 relative the cap body 115 of the pump assembly 112 upwardly and inwardly in a retraction stroke to the retracted position shown in FIG. 5 thereby dispensing the fluid product 14 downwardly onto the user's hand 620. On release of the lower handle end of the lever 610, a spring 622 biases the upper end of the lever 610 downwardly so that the lever 610 moves the piston-forming element 114 relative the piston chamber-forming cap body 115 outwardly in an extension stroke to an extended position not shown in FIG. 5.

A cover member 624 is hinged at 625 to an upper forward extension 626 of the back plate 604 so as to permit manual removal and replacement of the fluid storage reservoir 10.

FIGS. 5 and 7 show the fluid storage reservoir 10 and its pump assembly 112 of FIG. 5 in cross-sectional front view in which the piston-forming element 114 is in a retracted position relative to the cap body 115.

The cap body 115 has the end wall 123 supporting both a cylindrical inner tube 124 and a cylindrical outer tube 125 coaxial about a common central axis 126. The cylindrical inner tube 124 extends to an open inner end 127. The cylindrical outer tube 125 extends from the end wall 123 to an open inner end 128. The annular engagement flange 117 extends radially outwardly from the cylindrical outer tube 125.

A liquid chamber 130 is provided within the inner tube 124. At an inner end of the liquid chamber 130, an inlet opening 131 is provided in communication with the fluid product 14 within the first container 11. A one-way liquid valve 332 is disposed across the inlet opening 131 to provide for fluid product 14 to flow from the first container 11 into the liquid chamber 130 yet to prevent fluid product 14 to flow from the liquid chamber 130 to the first container 11 by reason of the one-way inlet valve 131 carrying a resilient valve disc 133 which engages a radially inwardly directed inner wall 134 of the inner tube 124.

The piston-forming element 114 carries a liquid piston 135 coaxially disposed within the liquid chamber 130. The piston-forming element 114 is coaxially slidable relative to the piston chamber-forming body 115 about the axis 126 for movement in a cycle of operation including a retraction stroke and an extension stroke. In an extension stroke, the liquid piston 135 of the piston-forming element 114 moves from the retracted position of FIG. 6 axially outwardly to an extended position not shown. In a retraction stroke, the liquid piston 135 of the piston-forming element 114 moves from the extended position to the retracted position of FIG. 6.

In the extension stroke, axial outward movement of the liquid piston 135 draws the fluid product 14 from the first container 11 through the inlet opening 131 past the one-way valve 333 into the liquid chamber 130. In the retraction stroke, axial inward movement of the liquid piston 135 forces the fluid product 14 from the liquid chamber 130, past a flexible inner disc 136 into an annular space 137 about a hollow piston stem 138 of the liquid piston 135 between the flexible inner disc 136 and an outer sealing disc 139, through a radially extending port 140 into a central passageway 141 within the piston stem 138 to the discharge outlet 120. The piston pump assembly 112 operates in an analogous manner to the piston pumps disclosed in U.S. Pat. No. 5,282,552 to Ophardt, issued Feb. 1, 1994, the disclosure of which is incorporated by reference.

Figure 8:
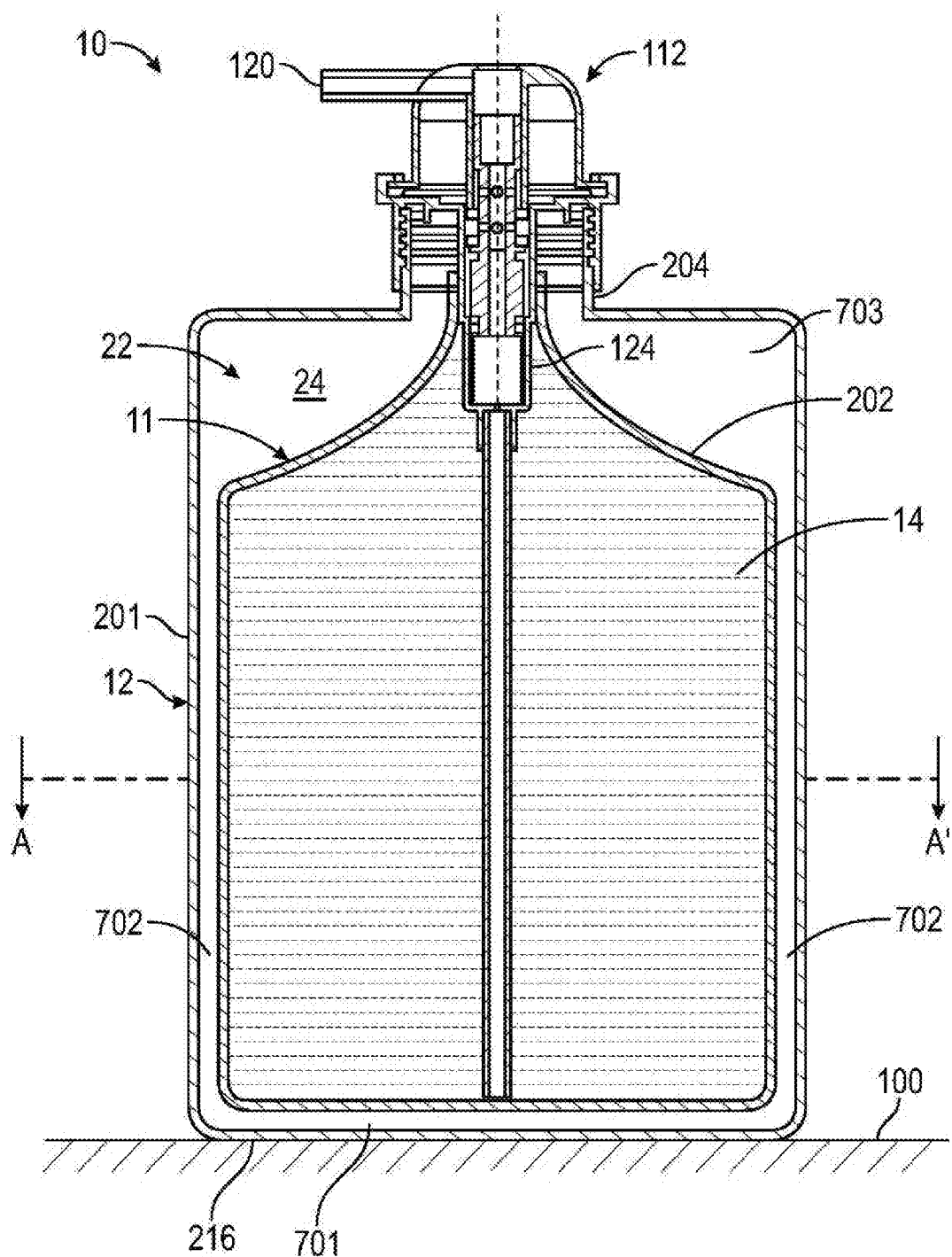
FIG. 8 is a cross-sectional front view of a third embodiment of a fluid storage reservoir in accordance with the present invention.
Figure 9:
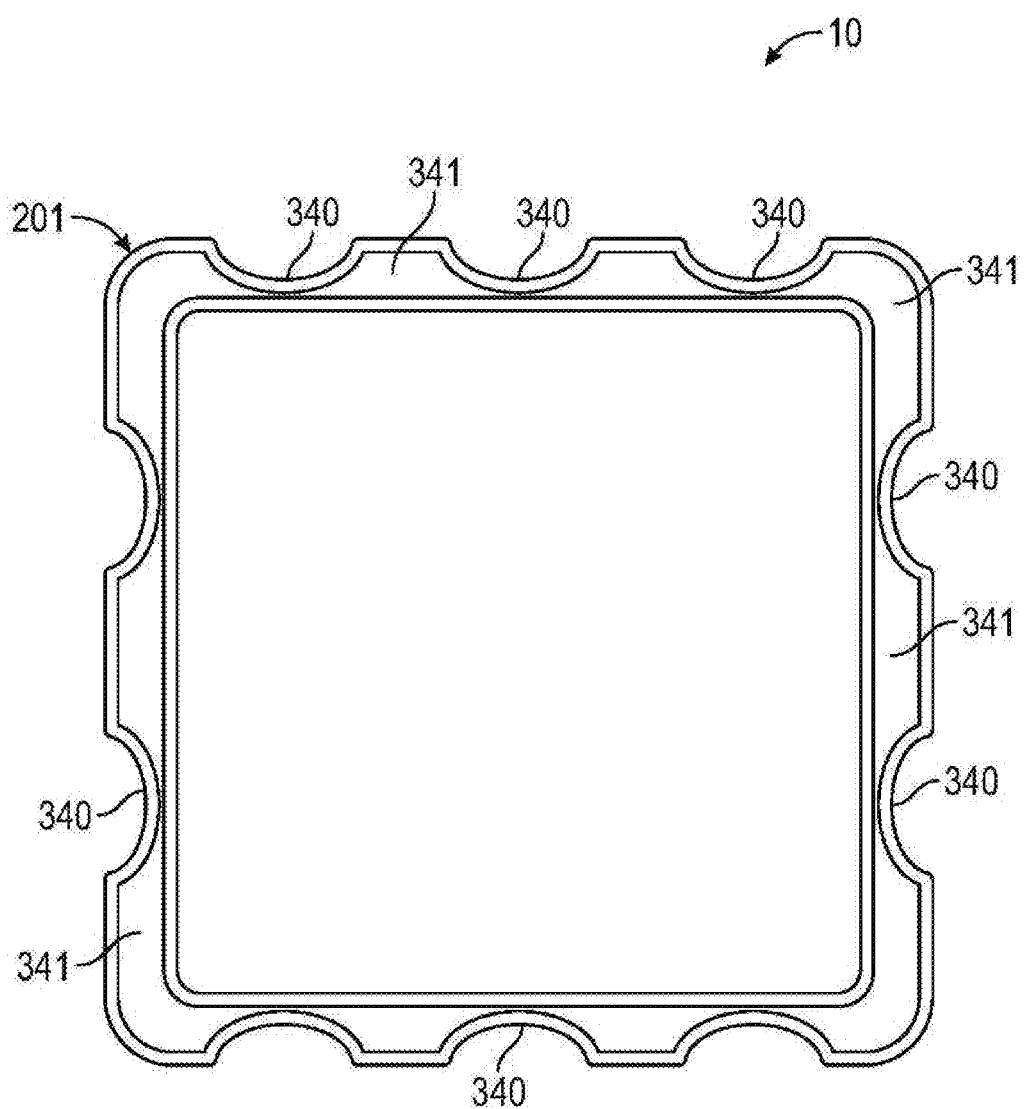
FIG. 9 is a cross-sectional plan view of the fluid storage reservoir of FIG. 8 along section line A-A' on FIG. 8.
Figure 10:
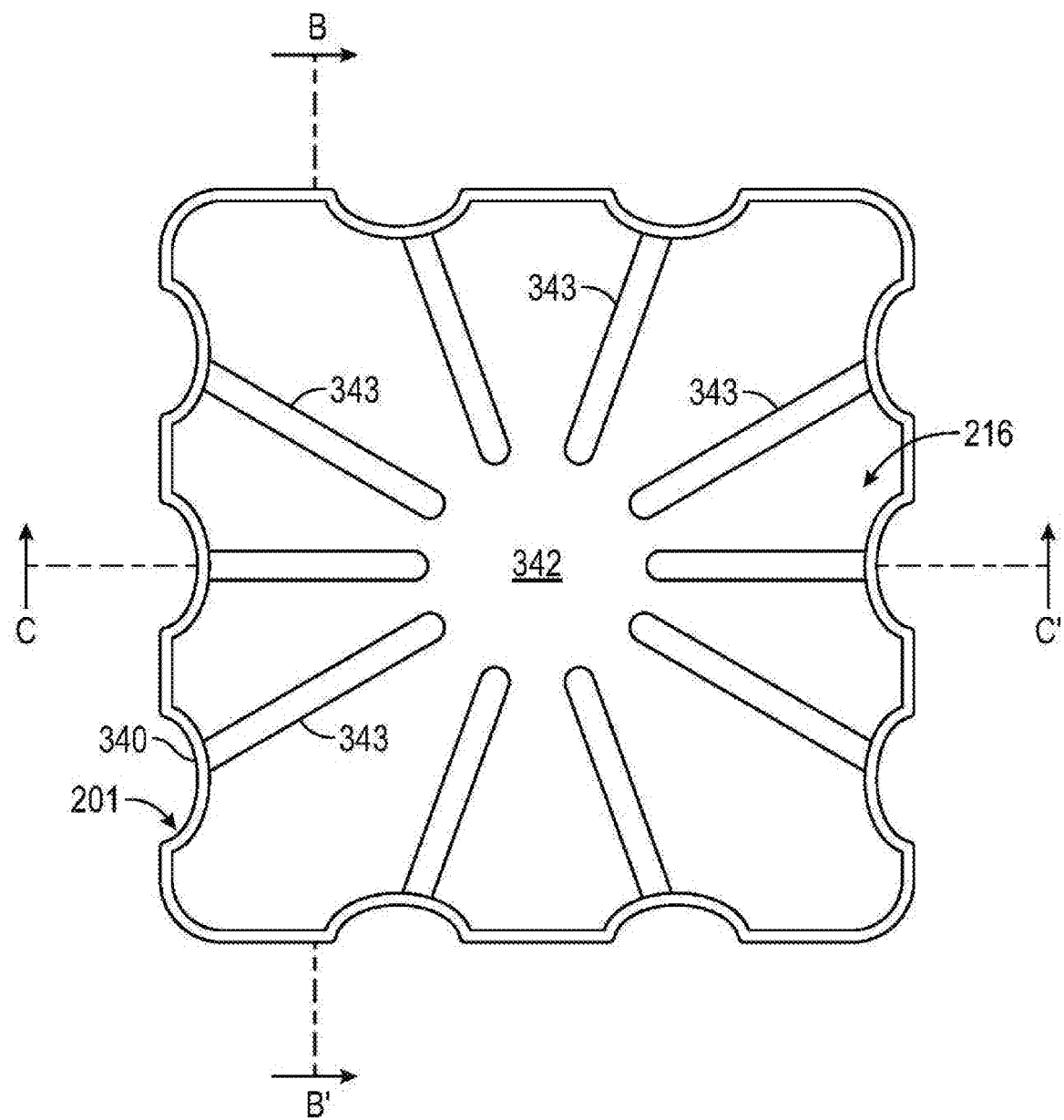
FIG. 10 is a cross-sectional plan the same as in FIG. 9 but with an inner bag removed.
Figure 11:
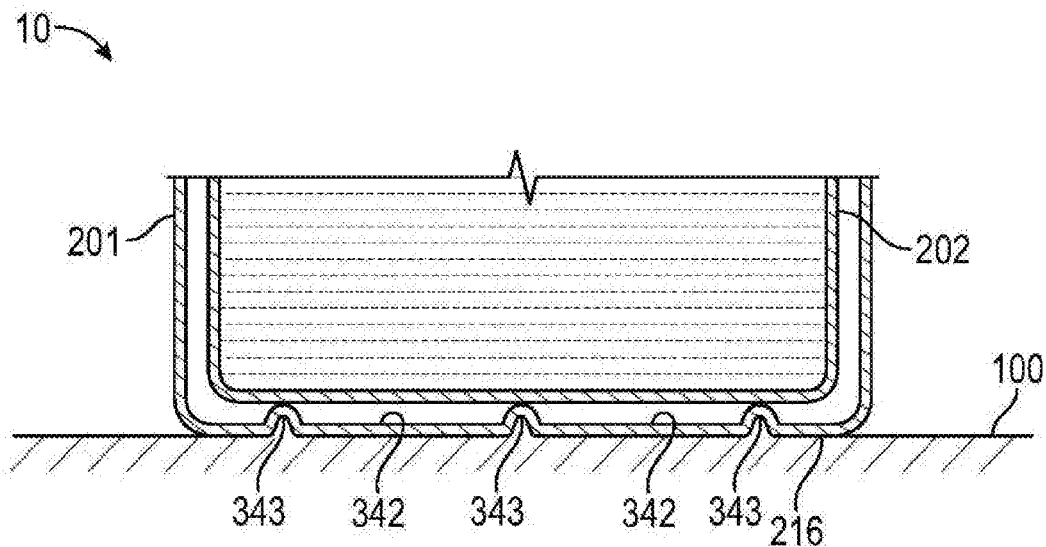
FIG. 11 is a cross-sectional side view of the fluid storage reservoir of FIG. 8 along section line B-B' on FIG. 8.
Figure 12:
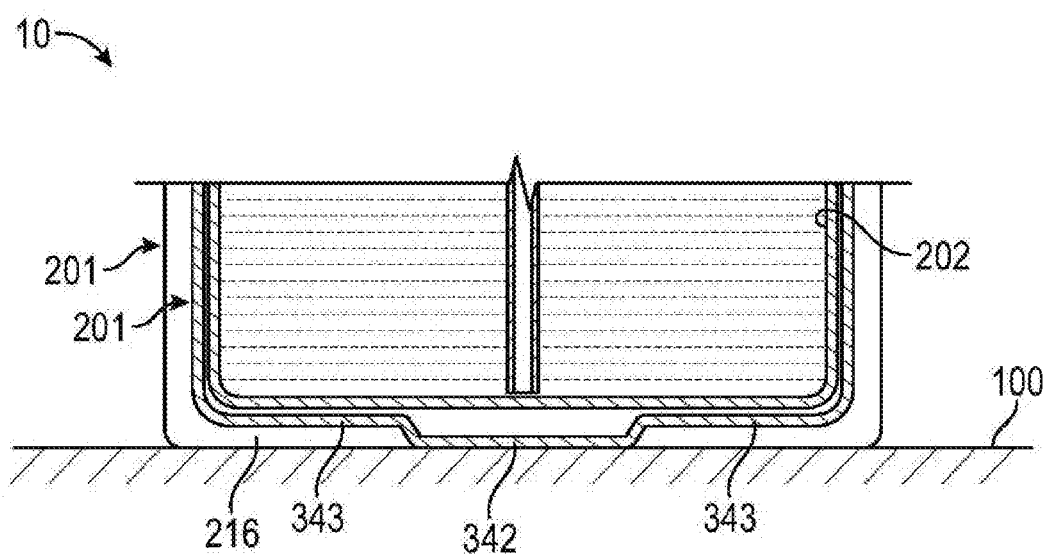
FIG. 12 is a cross-sectional front view of the fluid storage reservoir of FIG. 8 along section line C-C' on FIG. 8.

Reference is made to FIGS. 8 to 12 which show a third embodiment of a fluid storage reservoir 10 in accordance with the present invention. The fluid storage reservoir 10 includes a rigid outer bottle 201 and a flexible inner bag 202. A pump assembly 112 that includes both a liquid pump and an air pump is threadably engaged on a threaded neck of the rigid bottle 201 and is adapted to draw the product 14 from the bag 210 and dispense it from an outlet 120 as a foam of the product 14 mixed with air. The pump assembly 112 is the same as that disclosed in U.S. Patent Publication US 2017/0266680 to Ophardt et al, published Sep. 21, 2017, the disclosure of which is incorporated herein by reference. The flexible bag 202 is enclosed but for an opening which is heat sealed about an inner tube 124 of the pump assembly 112 that extends downwardly inside the neck 204 of the bottle 201. The pump assembly 112 has a piston biased to an extended position as shown in FIG. 8 in which product 14 is prevented from discharge from the first container 11 and in which flow into or out of the second container 21 is prevented. After storage, during operation of the pump assembly 112 to dispense the product 14 from within the first container 11, during operation of the pump assembly 112, a one-way valve mechanism is provided that opens to relieve any vacuum created within the second container 21 to avoid creating a vacuum which would impede the collapse of the collapsible bag 202. The rigid bottle is adapted to be self-supporting on its second end wall 216 as on a support surface 100. As can be seen in FIGS. 8 and 9, the first container 11 and notably its bag 202 is spaced inwardly from the wall of the second container 21 and notably the wall of the rigid bottle 201 with spaces therebetween including a space 701 at the bottom between the second end walls of the bag 202 and the second end wall 216 of the bottle 201, a space 702 between the circumferential walls of the bag 202 and the circumferential walls of the bottle 201 and an annular space 703 about the upper end of the bag 202. Towards ensuring there are spaces provided which separate the walls of the bag 202 from the walls of the bottle 201, the rigid bottle 201 is shown as being provided with a series of circumferentially spaced, vertically extending channel ways 340 in its circumferential side walls which assist in holding the circumferential walls of the inner bag 202 spaced inwardly providing vertically extending passageways 341 to receive and permit flow of the sacrifice fluid. Similarly, as can be seen in FIGS. 10, 11 and 12, the second end wall 216 of the bottle 201 is provided with a flat floor portion 342 from which a number of ridges 343 extend upwardly so as to provide, as seen in FIGS. 11 and 12, a vertical spacing between the bottom wall of the bag 202 and the second end wall 216 of the bottle 201.

Figure 13:
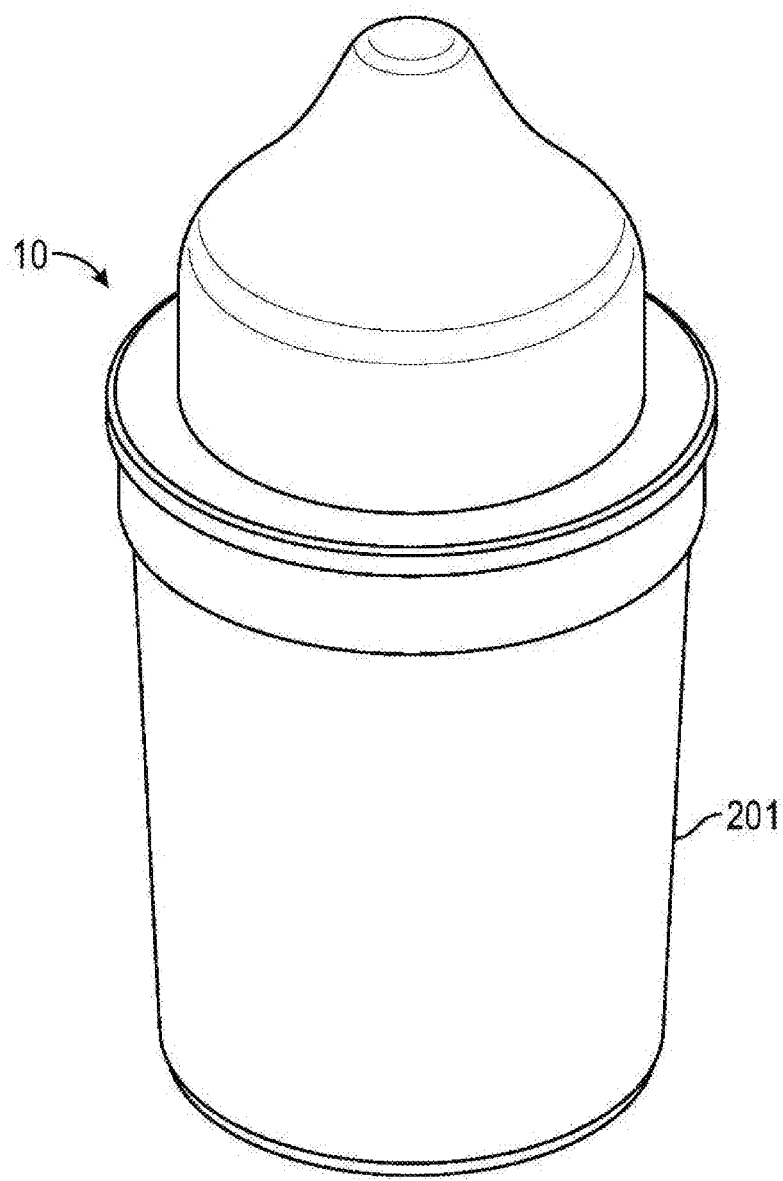
FIG. 13 is a pictorial view of a fourth embodiment of a fluid storage reservoir in accordance with the present invention including a removable cap.
Figure 14:
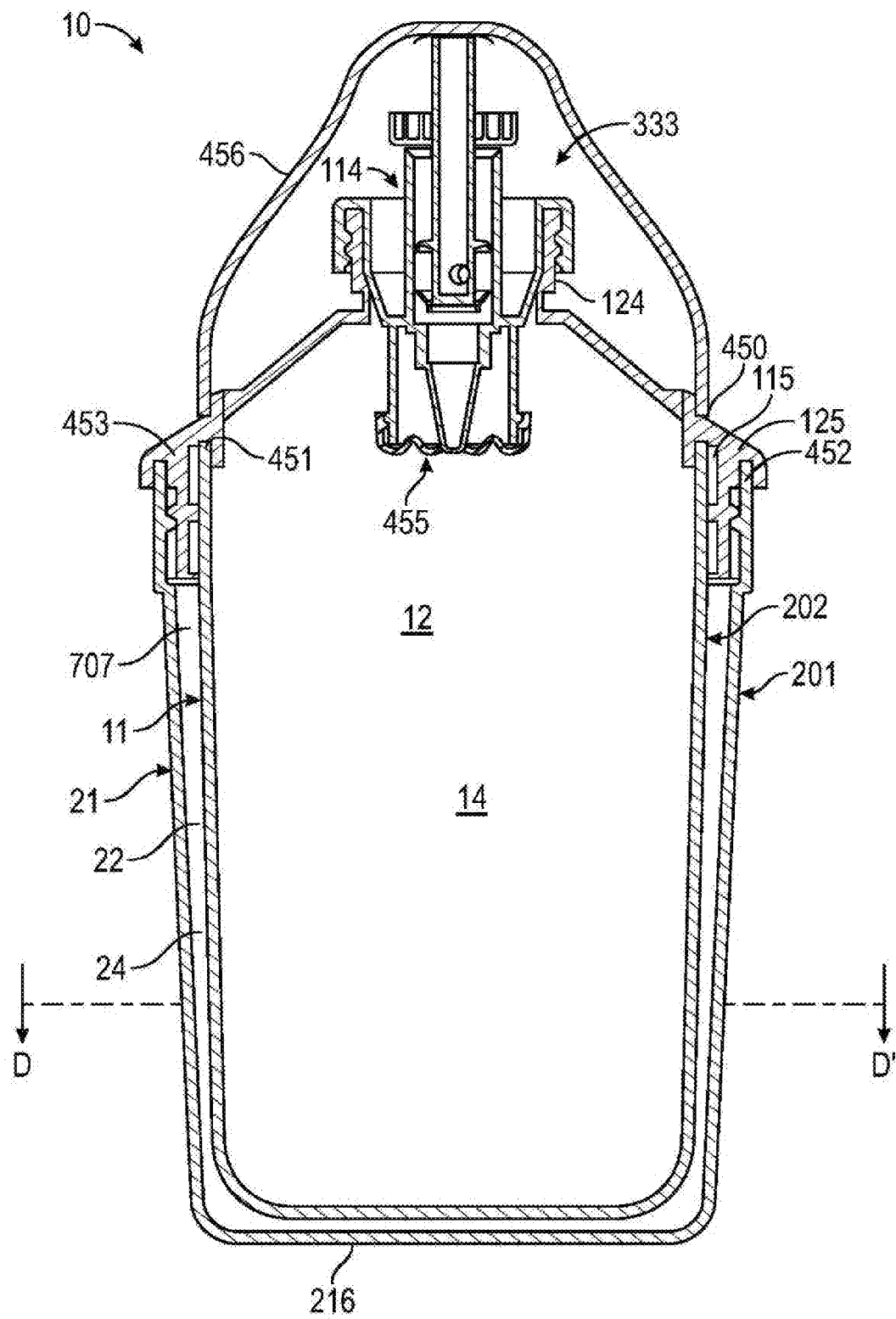
FIG. 14 is a cross-sectional front view of the fluid storage reservoir and cap in FIG. 13.
Figure 15:
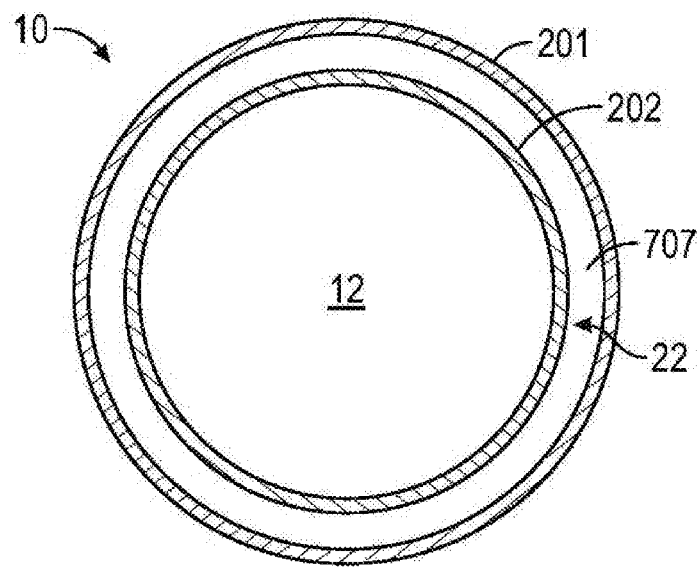
FIG. 15 is a cross-sectional plan view of the fluid storage reservoir in FIG. 13 along section line D-D' on FIG. 14.

Reference is made to FIGS. 13 to 15 which illustrate a fourth embodiment of a fluid storage reservoir 10 in accordance with the present invention. As seen in cross-section in FIG. 14, a fluid reservoir bottle is formed by a cap 115, an inner bottle 202 and an outer bottle 201. The inner bottle 202 has an open upper end 450 which is received in sealed engagement within a downwardly facing channel 451 in the cap 115. The outer bottle 201 also has an open upper end 452 which is received in a downwardly opening groove 453 in an outer tube 125 of the cap 115. The cap 115 carries a threaded center tube 124. A pump assembly 112 is threadably engaged on the threaded center tube 124 and comprises a piston pump 114 similar to that described in U.S. Pat. No. 7,815,076 to Ophardt, issued Oct. 19, 2010 with a one-way vacuum relief valve 455 to permit atmospheric air to enter the first container 11 if a sufficient vacuum is created within the interior 12 of the first container 11. A removable closure cap 456 is provided that sealably engages annularly about the cap 115. The first container 11 is defined within the inner bottle 202, the cap 115 and the pump assembly 112. The outer container 21 is defined between the inner bag 201 and the outer bag 202 closed at an upper end by the body 115. As can be seen in FIG. 15, in cross-section, an annular space is provided between the walls of the inner bottle 202 and the walls of the outer bottle 201 which annular space 707 forms the second container 21. Each of the outer bottle 201 and the inner bottle 202 preferably have a resiliency that permits the reservoir 10 to be self-supporting on a second end wall 216 of the outer bottle 201, however, preferably with the walls of the outer bottle 201 and the inner bottle being sufficiently resilient so as to collapse sufficiently to accommodate the loss of volume in the first container 11 and the second container 21 as the volatile component escapes to the atmosphere during a desired storage shelf life.

Figure 16:
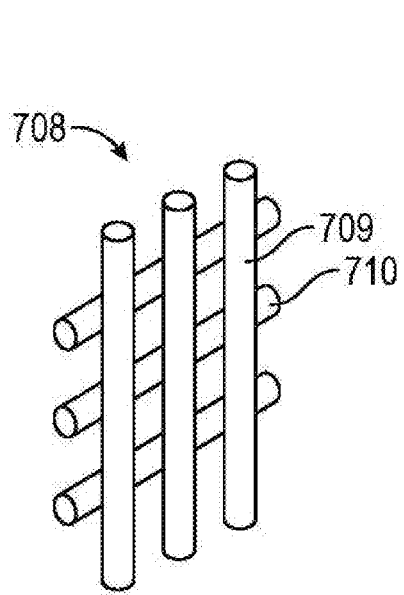
FIG. 16 is a pictorial view of a portion of a screen spacing member.
Figure 17:
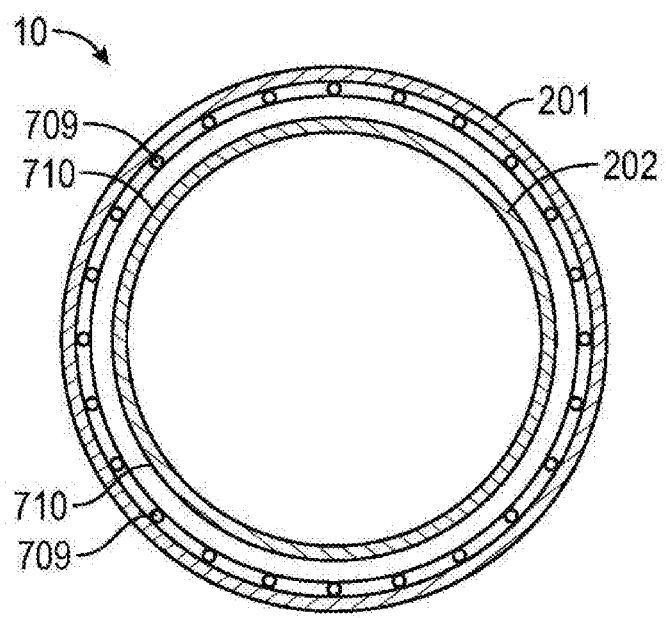
FIG. 17 is a cross-sectional plan view of the fluid storage reservoir as in FIG. 15 but with the screen spacing member of FIG. 16 in the annular space outside a first container and within a second container.

Reference is made to FIG. 16 which illustrates a small section of a spacing screen member 708 made up of crisscrossing rod-like members 709 and 710 which is adapted to optionally be placed so as to extend annularly within the annular space between the inner bag 201 and the outer bag 202 as schematically illustrated in the cross-section of FIG. 17 towards assisting in maintaining the space 707 between the outer bottle 201 and the inner bottle 202 as is advantageous to have sacrifice liquid 24 maintained consistently throughout the height of the first container 11 and second container 21.

Figure 18:
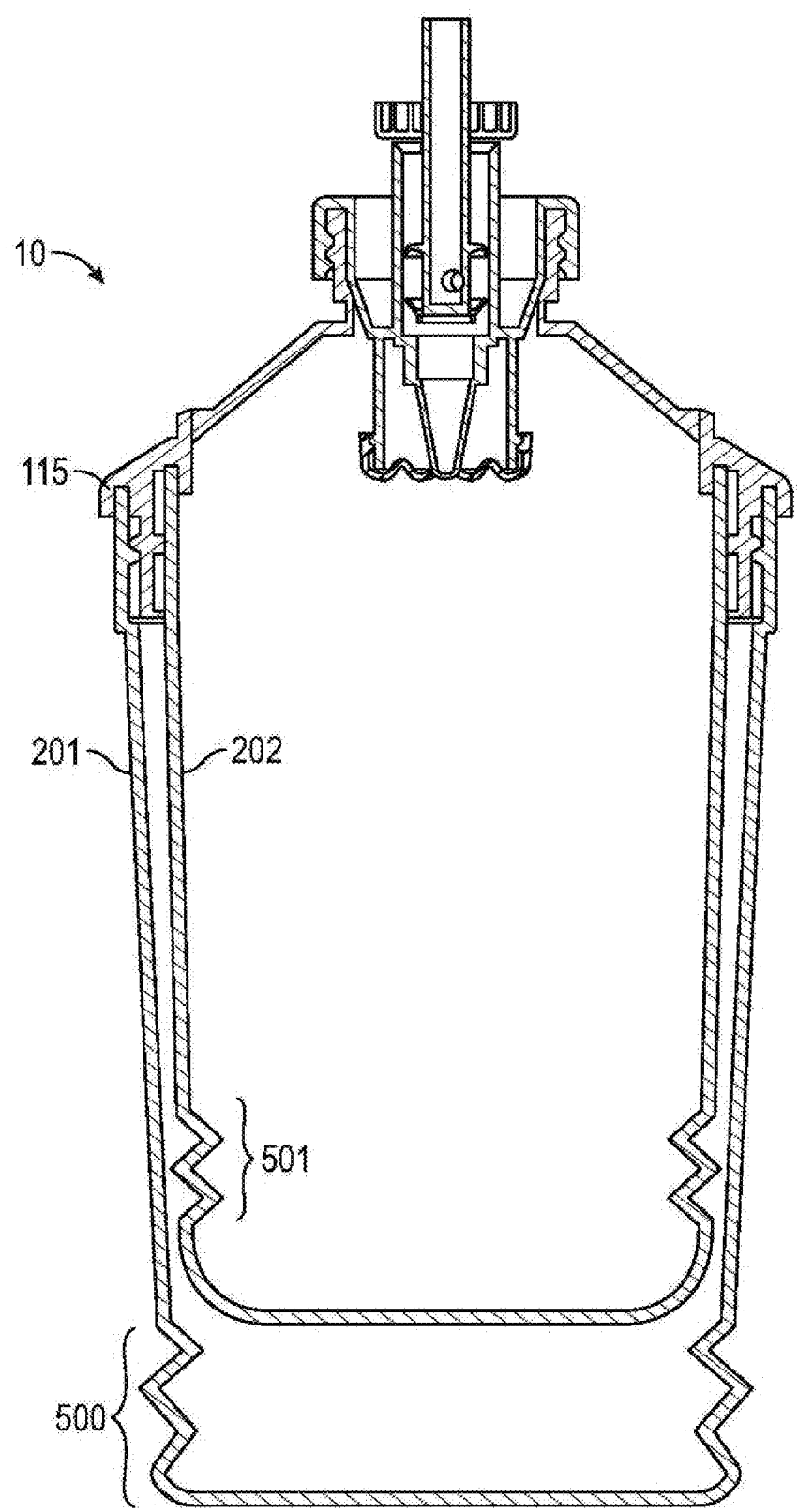
FIG. 18 is a cross-sectional front view of a fluid storage reservoir in accordance with a fifth embodiment of the present invention.

Reference is made to FIG. 18 which shows a fifth embodiment of a fluid storage reservoir 10 in accordance with the present invention and which is identical to the embodiment illustrated in FIGS. 13 to 15 but for the first exception that a bellows portion 500 of the circumferential side wall of the outer bottle 201 is formed as a bellows and a bellows portion 501 of the circumferential side wall of the inner bag 202 is also formed as a bellows. Each bellows portion 500 and 501 is adapted to compress and expand axially to accommodate changes in volumes of the first container 11 and the second container 21. The bellows portions 500 and 501 permit the outer bottle 201 and the inner bottle 202 to be formed to be substantially rigid other than over the bellows portions.

While the invention has been described with reference to preferred embodiments, many modifications and variations will now occur to a person skilled in the art. For a definition of the invention, reference is made to the accompanying claims.

I claim:

1. A method of storing a product containing an initial concentration of a volatile component to increase shelf life of the product, the method comprising:
storing the product in an enclosed first container defining an enclosed first interior within a first enclosing wall member having an inner surface of the first enclosing wall member open into the first interior and an opposed outer surface of the first enclosing wall member,
providing a transfer segment of the first enclosing wall member over which the outer surface is in contact with a sacrifice material containing the volatile component in an initial concentration in the sacrifice material, the transfer segment having a first permeability that permits passage of the volatile component to the first interior of the first container through the first enclosing wall member from the outer surface to the inner surface,
providing an escape segment of the first enclosing wall member over which the outer surface is in contact with atmosphere with the inner surface in contact with the product in the first interior of the first container, the escape segment having a second permeability that permits passage of the volatile component from the first interior of the first container through the first enclosing wall member of the first container from the inner surface to the outer surface.

2. The method as claimed in claim 1 wherein the transfer segment having a third permeability that permits passage of the volatile component from the first interior of the first container through the first enclosing wall member from the inner surface to the outer surface.

3. The method as claimed in claim 1 wherein the initial concentration of the volatile component in the sacrifice material is equal to or greater than the initial concentration of the volatile component in the product.

4. The method as claimed in claim 3 wherein the volatile component is an alcohol and the product is a cleaning composition.

5. The method as claimed in claim 4 wherein the product is an alcohol based surface disinfectant containing at least 40% of an alcohol as the volatile component,
the sacrifice material comprises a solution of the alcohol having the alcohol in a percentage at least as great as the said percent of the alcohol in the alcohol based surface disinfectant.

6. The method as claimed in claim 4 wherein the volatile component is an alcohol and the product is a cleaning composition.

7. A method of storing a product containing an initial concentration of a volatile component to increase shelf life of the product, the method comprising:
storing the product in an enclosed first container defining an enclosed first interior within a first enclosing wall member having an inner surface of the first enclosing wall member open into the first interior and an opposed outer surface of the first enclosing wall member,
providing a second container defining an enclosed second interior within a second enclosing wall member having an inner surface and an opposed outer surface,
providing a sacrifice material in the second interior of the second container in contact with the inner surface of the second enclosing wall member, the sacrifice material containing the volatile component in an initial concentration,
providing a transfer segment of the first enclosing wall member -to define at least in part the second interior of the second container such that the outer surface of the first enclosing wall member over the transfer segment is in contact with the sacrifice material in the second interior of the second container and the inner surface of the first enclosing wall member over the transfer segment is in contact with the product in the first interior of the first container
the transfer segment having a first permeability that permits passage of the volatile component from the second interior of the second container to the first interior of the first container through the first enclosing wall member from the outer surface of the first enclosing wall member to the inner surface of the first enclosing wall member,
providing an escape segment selected from the group consisting of:
(a) a first escape portion of the first enclosing wall member of the first container with over which the inner surface of the first enclosing wall member is in contact with the product and the outer surface the first enclosing wall member is in contact with the atmosphere,. with the first escape portion of the first enclosing wall member of the first container having a second permeability that permits passage of the volatile component through the first enclosing wall member of the first container from the first interior of the first container to the atmosphere, and
(b) a second escape portion of the second enclosing wall member of the second container over which the inner surface of the second enclosing wall member is in contact with the product and the outer surface of the second enclosing wall member is in contact with the atmosphere, the second escape portion of the second enclosing wall member of the second container having a third permeability that permits passage of the volatile component through the second enclosing wall member of the second container from the second interior of the second container to the atmosphere.

8. The method as claimed in claim 7 wherein:
selecting the initial concentration of the volatile component in the product and the initial concentration of the volatile component in the sacrifice material such that from an initial fill point of time when the first container is filled with the product and the second container is filled with the sacrifice material, a shelf life time during which the product maintains a concentration in excess of a minimum concentration of the volatile component is greater than a predetermined time having the regard to factors including:
i) relative surface areas of the transfer segment, the first escape portion and the second escape portion; and
ii) the permeability-of-the volatile component through each of the transfer segment, the first escape portion and the second escape portion; and
iii) the initial concentration of the volatile component in the product iv) the initial concentration of the volatile component in the sacrifice material.

9. The method as claimed in claim 7 wherein the initial concentration of the volatile component in the sacrifice material is equal to or greater than the initial concentration of the volatile component in the product.

10. The method as claimed in claim 7 wherein the volatile component is an alcohol and the product is a cleaning composition.

11. The method as claimed in claim 8 wherein the product is an alcohol based surface disinfectant containing at least 40% of an alcohol as the volatile component, the sacrifice material comprises a solution of the alcohol having the alcohol in a percentage at least as great as the said percent of the alcohol in the alcohol based surface disinfectant.

12. The method as claimed in claim 7 wherein the transfer segment of the first enclosing wall member is an intermediate transfer wall shared by both the first container and the second container.

13. The method as claimed in claim 7 wherein the transfer segment of the first enclosing wall member is an intermediate transfer wall shared by both the first container and the second container and forming part of the first enclosing wall member and part of the second enclosing wall member.

14. The method as claimed in claim 7 including providing the product in the first container to have as a desired shelf life time during which desired shelf life time the product maintains a concentration in excess of a desired minimum concentration of the volatile component,
the desired shelf life time is greater than a predetermined time from an initial fill point of time when the first container is filled with the product and the second container is filled with the sacrifice material,
the providing the product in the first container to have the desired shelf life time including the steps of:
selecting :
parameter (a): the initial concentration of the volatile component in the product,
parameter (b): the initial concentration of the volatile component in the sacrifice material,
parameter (c): a volume of the production of the first container at the initial fill point, and
parameter (d): a volume of the sacrifice material in the second container at the initial fill point as a function of:
i) surface areas of each of the transfer segment, the first escape segment and the second escape segment; and
ii) the permeability of the volatile component through each of the transfer segment, the first escape segment and the second escape segment.

15. The method as claimed in claim 14 wherein the selecting of:
parameters (a), (b), (c) and (d) is as a function of:
i) surface areas of each of the transfer segment, the first escape segment and the second escape segment;
ii) the permeability of the volatile component through each of the transfer segment, the first escape segment and the second escape segment, and
iii) temperature over time.

16. The method as claimed in claim 15 wherein the initial concentration of the volatile component in the sacrifice material is equal to or greater than the initial concentration of the volatile component in the product.

17. The method as claimed in claim 15 wherein the selecting of the parameters (a), (b), (c) and (d) includes estimating with time :
transfer of the volatile component between the first container and the second container, escape of the volatile component through the first escape portion from the first interior to the atmosphere, and
escape of the volatile component through the second escape portion from the second interior to the atmosphere.

18. The method as claimed in claim 17 wherein the product is an alcohol based surface disinfectant containing at least 40% of an alcohol as the volatile component,
the sacrifice material comprises a solution of the alcohol having the alcohol in a percentage at least as great as the said percent of the alcohol in the alcohol based surface disinfectant.

19. The method as claimed in claim 15 wherein the selecting of the parameters (a), (b), (c) and (d) includes
calculation of the concentration of volatile material in each of the product and the sacrifice material over time.

20. The method as claimed in claim 15 wherein the selecting of the parameters (a), (b), (c) and (d) includes
calculation of the concentration of volatile material in each of the product and the sacrifice material over time.

* * * * *